(12) United States Patent
Shinohara et al.

(10) Patent No.: US 11,207,044 B2
(45) Date of Patent: Dec. 28, 2021

(54) INFORMATION PROCESSING APPARATUS, INFORMATION PROCESSING METHOD, COMPUTER-READABLE MEDIUM, AND BIOLOGICAL SIGNAL MEASUREMENT SYSTEM

(71) Applicants: Michinari Shinohara, Kanagawa (JP); Yutaka Yagiura, Kanagawa (JP); Daisuke Sakai, Tokyo (JP)

(72) Inventors: Michinari Shinohara, Kanagawa (JP); Yutaka Yagiura, Kanagawa (JP); Daisuke Sakai, Tokyo (JP)

(73) Assignee: Ricoh Company, Ltd., Tokyo (JP)

( * ) Notice: Subject to any disclaimer, the term of this patent is extended or adjusted under 35 U.S.C. 154(b) by 498 days.

(21) Appl. No.: 16/038,227

(22) Filed: Jul. 18, 2018

(65) Prior Publication Data

US 2018/0325483 A1  Nov. 15, 2018

Related U.S. Application Data

(63) Continuation of application No. PCT/JP2018/009352, filed on Mar. 9, 2018.

(30) Foreign Application Priority Data

Mar. 17, 2017 (JP) .............................. JP2017-053716
Sep. 29, 2017 (JP) .............................. JP2017-191739

(51) Int. Cl.
*A61B 6/00* (2006.01)
*G06T 7/11* (2017.01)
(Continued)

(52) U.S. Cl.
CPC .............. *A61B 6/5211* (2013.01); *A61B 5/00* (2013.01); *A61B 5/24* (2021.01); *A61B 5/318* (2021.01);
(Continued)

(58) Field of Classification Search
CPC ....... A61B 6/5211; A61B 6/032; A61B 6/463; A61B 6/468; A61B 6/56; A61B 5/00;
(Continued)

(56) References Cited

U.S. PATENT DOCUMENTS 4,974,602 A     12/1990  Abraham-Fuchs et al.
2009/0287271 A1*  11/2009  Blum .................. G06K 9/00885
                                                                  607/45
(Continued)

FOREIGN PATENT DOCUMENTS

JP     H10-127592 A      5/1998
JP     2000-005133       1/2000
(Continued)

OTHER PUBLICATIONS

Machine Translation of JP2001275989A (Year: 2001).*
(Continued)

*Primary Examiner* — Amelie R Davis
*Assistant Examiner* — John Denny Li
(74) *Attorney, Agent, or Firm* — Harness, Dickey & Pierce, P.L.C.

(57) ABSTRACT

An information processing apparatus includes a display control unit. The display control unit is configured to perform control to display a signal source in a superimposed manner on a plurality of biological tomographic images sliced in a predetermined direction, the signal source corresponding to a part of biological data indicating a temporal change of a biological signal, and initially display, in a display region of a screen of a display unit, a biological tomographic image on which a predetermined signal source is superimposed among the plurality of sliced biological tomographic images.

20 Claims, 30 Drawing Sheets

(51) Int. Cl.
    *G06F 3/0481* (2013.01)
    *G06F 3/0482* (2013.01)
    *A61B 5/00* (2006.01)
    *A61B 6/03* (2006.01)
    *G06F 3/01* (2006.01)
    *A61B 5/24* (2021.01)
    *A61B 5/318* (2021.01)
    *A61B 5/369* (2021.01)
    *A61B 5/389* (2021.01)

(52) U.S. Cl.
    CPC .............. *A61B 5/369* (2021.01); *A61B 5/389* (2021.01); *A61B 6/032* (2013.01); *A61B 6/463* (2013.01); *A61B 6/468* (2013.01); *A61B 6/56* (2013.01); *G06F 3/015* (2013.01); *G06F 3/0482* (2013.01); *G06F 3/04817* (2013.01); *G06T 7/11* (2017.01); *G06T 2207/10088* (2013.01); *G06T 2207/30016* (2013.01)

(58) Field of Classification Search
    CPC ....... A61B 5/04; A61B 5/0402; A61B 5/0476; A61B 5/0488; G06T 7/11; G06T 2207/10088; G06T 2207/30016; G06F 3/015; G06F 3/04817; G06F 3/0482
    See application file for complete search history.

(56) References Cited

U.S. PATENT DOCUMENTS

| | | |
|---|---|---|
| 2009/0287272 A1 | 11/2009 | Kokones et al. |
| 2009/0287273 A1 | 11/2009 | Carlton et al. |
| 2009/0287467 A1 | 11/2009 | Sparks et al. |
| 2010/0049276 A1 | 2/2010 | Blum et al. |
| 2011/0313268 A1 | 12/2011 | Kokones et al. |
| 2011/0313487 A1 | 12/2011 | Kokones et al. |
| 2012/0265267 A1 | 10/2012 | Blum et al. |
| 2012/0271376 A1 | 10/2012 | Kokones et al. |
| 2013/0096408 A1 | 4/2013 | He et al. |
| 2013/0226261 A1 | 8/2013 | Sparks et al. |
| 2014/0303486 A1 | 10/2014 | Baumgartner et al. |
| 2014/0316248 A1* | 10/2014 | deCharms ............ A61B 5/0048 600/411 |
| 2015/0297893 A1 | 10/2015 | Kokones et al. |
| 2016/0206380 A1 | 7/2016 | Sparks et al. |
| 2016/0345925 A1* | 12/2016 | Westerhoff ............ A61B 6/032 |

FOREIGN PATENT DOCUMENTS

| | | |
|---|---|---|
| JP | 2001-170018 A | 6/2001 |
| JP | 2001-275989 | 10/2001 |
| JP | 2018-089336 | 6/2018 |

OTHER PUBLICATIONS

International Search Report dated May 28, 2018 in PCT/JP2018/009352 filed Mar. 9, 2018.
Japanese Office Action dated Jun. 8, 2021 for corresponding Japanese Application No. 2017-191739.

\* cited by examiner

FIG.7

Annotation List

☑ Show Markup on wave ——————— 180a

| No. | File | Time | Event | MEMO | Cluster |
|---|---|---|---|---|---|
| 2 ☐ | 001 | 00:09:30 | 🔥 | normal spike | B |
| 1 ☐ | 001 | 00:05:00 | 🔥 | strong spike | A |
| 0 ☐ | 000 | 00:00:00 | 🔥 | Dr.memo | A |

Exit Measurement

180

INFORMATION PROCESSING APPARATUS, INFORMATION PROCESSING METHOD, COMPUTER-READABLE MEDIUM, AND BIOLOGICAL SIGNAL MEASUREMENT SYSTEM

CROSS-REFERENCE TO RELATED APPLICATIONS

The present application is a continuation application of International Application No. PCT/JP2018/009352, filed Mar. 9, 2018, which claims priority to Japanese Patent Application No. 2017-053716, filed Mar. 17, 2017, and Japanese Patent Application No. 2017-191739, filed Sep. 29, 2017. The contents of these applications are incorporated herein by reference in their entirety.

BACKGROUND OF THE INVENTION

1. Field of the Invention

The present invention relates to an information processing apparatus, an information processing method, a computer-readable medium, and a biological signal measurement system.

2. Description of the Related Art

Conventionally, there has been known a technique of displaying a signal source inside a living body, estimated based on a measured biological signal of a subject, on a tomographic image in a superimposed manner and displaying waveforms of a biological signal corresponding to the signal source in parallel on a screen (see, for example, Japanese Laid-open Patent Publication No. 2000-5133). In this technique, when an operator designates a desired time of the waveform of the displayed biological signal, display to specify a corresponding signal source position on the tomographic image is performed.

For example, a magnetoencephalography meter or an electroencephalograph that measures nerve activity of a brain discriminates a waveform point (hereinafter referred to as a singularity) peculiar to epilepsy from the measured waveform, estimates a signal source based on the singularity, and displays the signal source on a tomographic image in a superimposed manner. Then, a position to be excised by surgery (a point causing the epilepsy) is specified based on a position or the like of the signal source on the tomographic image.

In the conventional technique, however, there is a problem that the accuracy of specifying a target point which causes a case is not sufficient.

SUMMARY OF THE INVENTION

According to one aspect of the present invention, an information processing apparatus includes a display control unit. The display control unit is configured to perform control to display a signal source in a superimposed manner on a plurality of biological tomographic images sliced in a predetermined direction, the signal source corresponding to a part of biological data indicating a temporal change of a biological signal, and initially display, in a display region of a screen of a display unit, a biological tomographic image on which a predetermined signal source is superimposed among the plurality of sliced biological tomographic images.

BRIEF DESCRIPTION OF THE DRAWINGS

FIG. 7 is a view of an updated annotation list;

The accompanying drawings are intended to depict exemplary embodiments of the present invention and should not be interpreted to limit the scope thereof. Identical or similar reference numerals designate identical or similar components throughout the various drawings.

DETAILED DESCRIPTION OF THE PREFERRED EMBODIMENTS

Figure 1:
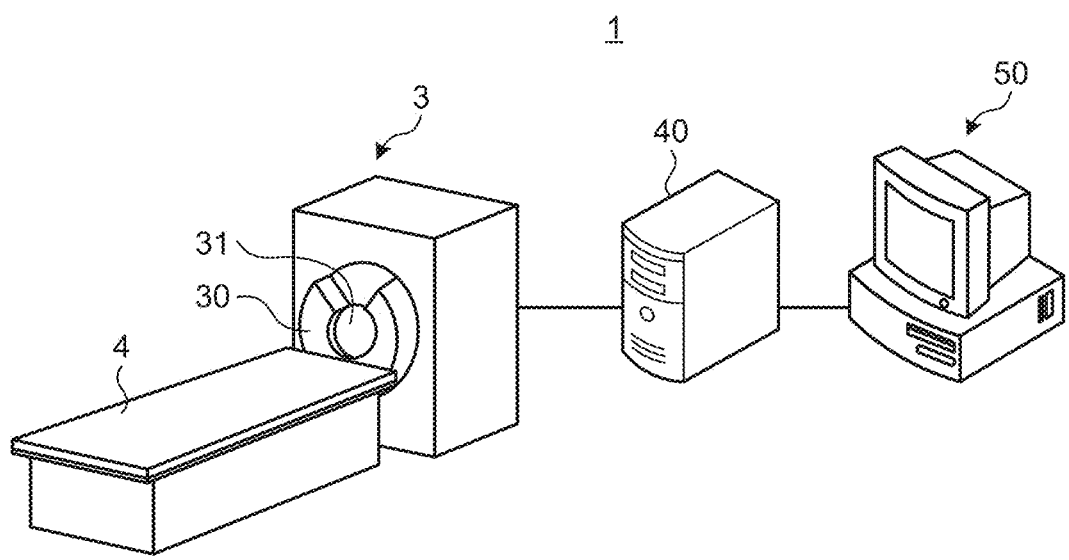
FIG. 1 is a schematic view of a biological signal measurement system according to an embodiment.

The terminology used herein is for the purpose of describing particular embodiments only and is not intended to be limiting of the present invention.

As used herein, the singular forms "a", "an" and "the" are intended to include the plural forms as well, unless the context clearly indicates otherwise.

In describing preferred embodiments illustrated in the drawings, specific terminology may be employed for the sake of clarity. However, the disclosure of this patent specification is not intended to be limited to the specific terminology so selected, and it is to be understood that each specific element includes all technical equivalents that have the same function, operate in a similar manner, and achieve a similar result.

An embodiment has an object to provide an information processing apparatus, an information processing method, a computer-readable medium, and a biological signal measurement system capable of improving the accuracy of specifying a target point that causes a case.

Hereinafter, embodiments of an information processing apparatus, an information processing method, a program, and a biological signal measurement system according to the present invention will be described in detail with reference to the accompanying drawings.

First Embodiment

FIG. 1 is a schematic view of a biological signal measurement system 1 according to the present embodiment. The biological signal measurement system 1 measures and displays a plurality of types of biological signals of a subject, for example, a magneto-encephalography (MEG) signal and an electro-encephalography (EEG) signal. The biological signal to be measured is not limited to the MEG signal and the EEG signal, and may be, for example, an electric signal (an electric signal that can be expressed as an electrocardiogram) generated depending on the activity of the heart. As illustrated in FIG. 1, the biological signal measurement system 1 includes a measurement device 3 that measures one or more biological signals of the subject, a server 40 that records the one or more biological signals measured by the measurement device 3, and an information processing apparatus 50 that analyzes the one or more biological signals recorded in the server 40. Although the server 40 and the information processing apparatus 50 are described separately herein, a mode, for example, in which at least some functions of the server 40 are incorporated in the information processing apparatus 50 may be provided.

In the example of FIG. 1, the subject (measured subject) lies on his back on a measurement table 4 with electrodes (or sensors) for EEG measurement attached to the head, and inputs the head portion into a cavity 31 of a Dewar flask 30 of the measurement device 3. The Dewar flask 30 is a holding container of cryogenic environment using liquid helium, and a large number of magnetic sensors for MEG measurement are arranged inside the cavity 31 of the Dewar flask 30. The measurement device 3 collects EEG signals from the electrodes and MEG signals from the magnetic sensors and outputs data (sometimes referred to as "measurement data" in the following description) including the collected EEG signals and MEG signals to the server 40. The measurement data recorded in the server 40 is read, displayed, and analyzed by the information processing apparatus 50. In general, the Dewar flask 30 including the magnetic sensors incorporated therein and the measurement table 4 are arranged in a magnetic shield room, but the magnetic shield room is not illustrated for convenience of illustration.

The information processing apparatus 50 displays waveforms of the MEG signals from the plurality of magnetic sensors and waveforms of the EEG signals from the plurality of electrodes in synchronization with each other on the same time axis. The EEG signal represents electrical activity of a nerve cell (flow of an ionic charge that occurs in a neuronal dendrite during synaptic transmission) as a voltage value between electrodes. The MEG signal represents a minute magnetic field fluctuation caused by electric activity of the brain. The brain magnetic field is detected by a highly-sensitive superconducting quantum interference device (SQUID) sensor. These EEG signals and MEG signals are examples of the "biological signal".

Figure 2:
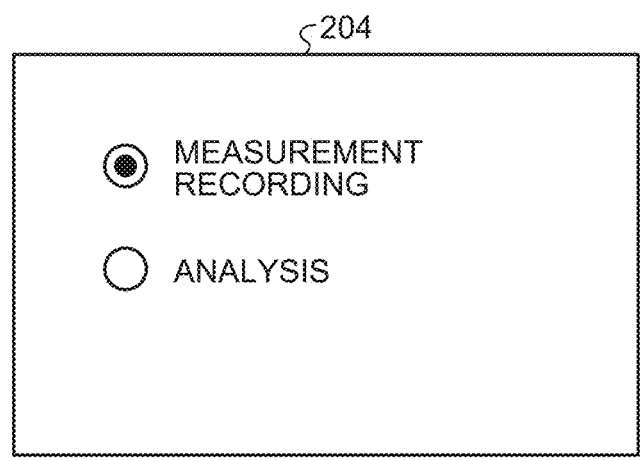
FIG. 2 is a view illustrating an example of a start screen displayed on an information processing apparatus.

FIG. 2 illustrates an example of a start screen 204 displayed on the information processing apparatus 50. On the start screen 204, selection buttons of "measurement recording" and "analysis" are displayed. In the case of an EEG and/or MEG measurement, measurement recording of data and analysis of data are often performed by different people. For example, when the "measurement recording" button is selected by a measuring technician (measurer), data measured by the measurement device 3 are sequentially stored in the server 40 and read out and displayed by the information processing apparatus 50. When the "analysis" button is selected by a doctor after the end of measurement recording, the recorded measurement data is read out and analyzed.

<Operation during Measurement Recording>

Figure 3:
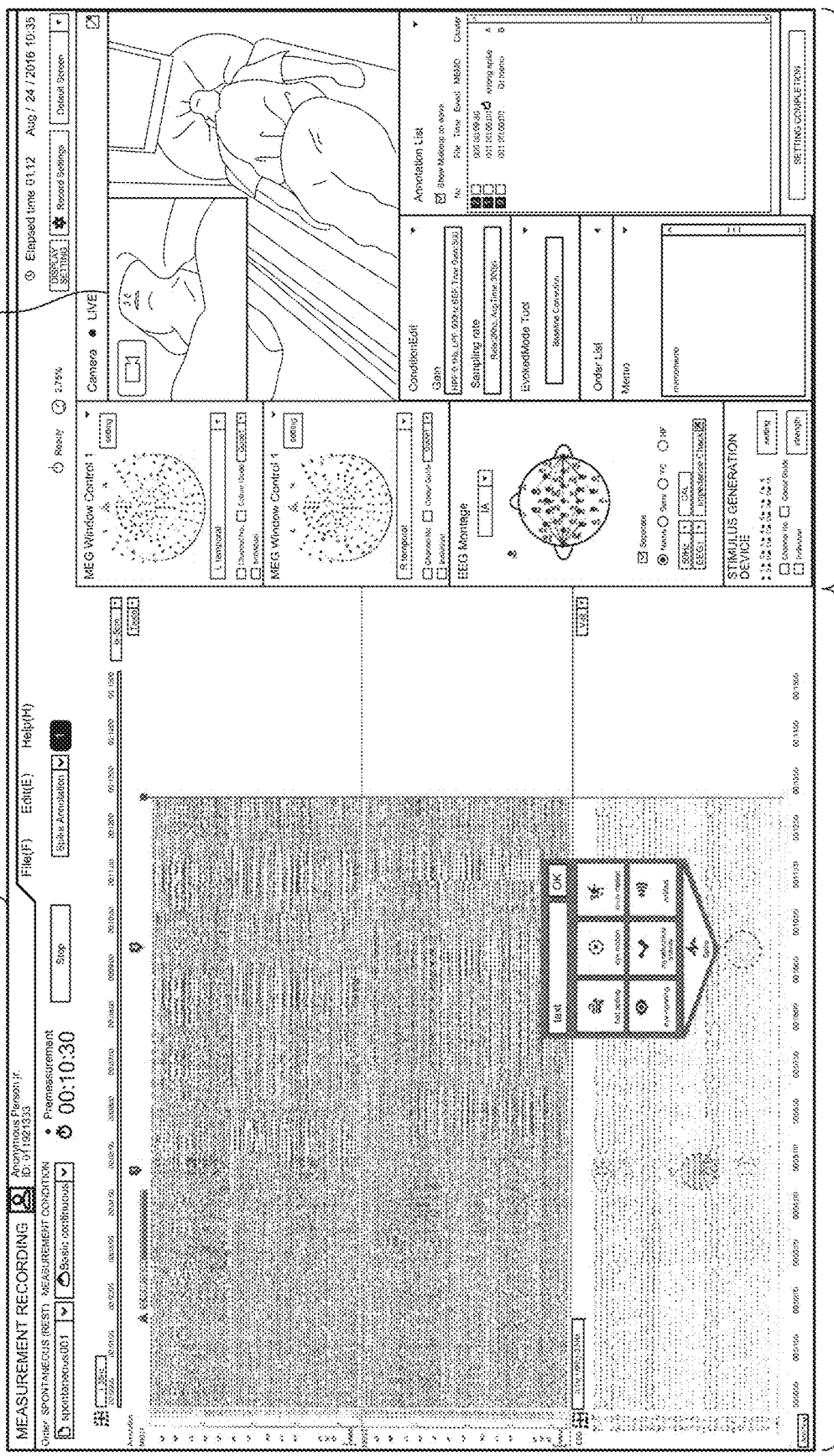
FIG. 3 is a view illustrating an example of a measurement recording screen.

FIG. 3 illustrates an example of a measurement recording screen. The "measurement recording" screen is displayed on a tab 111 on the screen. The measurement recording screen has a region 201A to display a measured signal waveform and a region 201B to display monitor information other than the signal waveform. The region 201A to display the signal waveform is arranged on the left side of the screen as viewed from the measurer and the region 201B to display the monitor information other than the signal waveform is arranged on the right side of the screen as viewed from the measurer. There is no waste in movement of gaze of the measurer in accordance with movement of the waveform detected and displayed in real time (displayed from the left side to the right side of the screen) and movement at the time of moving a mouse from the region 201A on the left side of the screen to the region 201B on the right side so that work efficiency improves.

A monitor window 170, configured to confirm a state of a subject during a measurement is displayed in the region 201B of the display screen. It is possible to improve reliability of a check and determination of the signal waveform by displaying a live image of the subject during the measurement, as will be described later. FIG. 3 illustrates a case where the entire measurement recording screen is displayed on the display screen of one monitor display (a display device 28 to be described later), but the region 201A on the left side and the region 201B on the right side may be displayed separately on two or more monitor displays.

Figure 4:
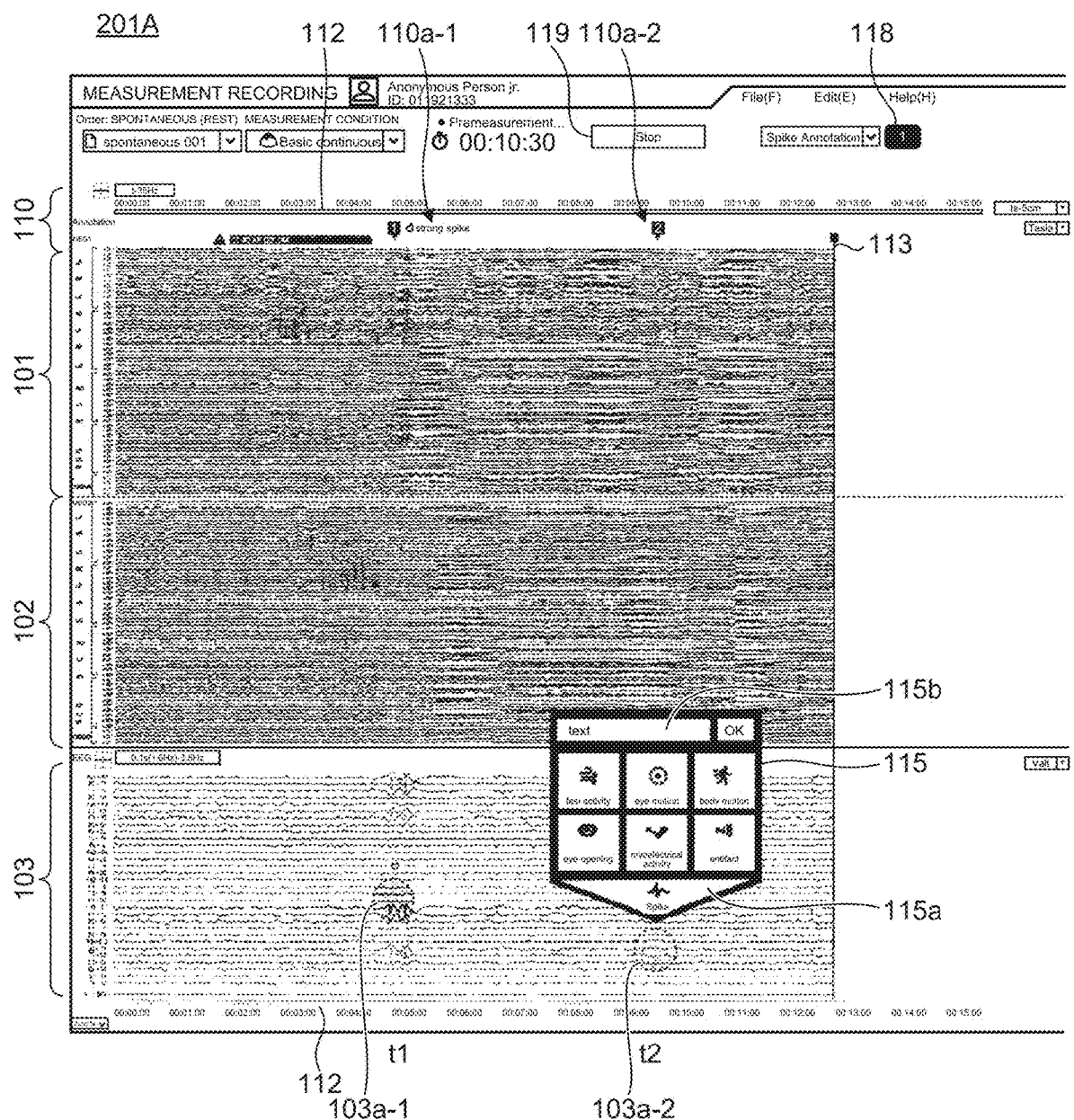
FIG. 4 is an enlarged view of a region on the left side of the measurement recording screen.

FIG. 4 is an enlarged view of the region 201A on the left side of FIG. 3. The region 201A includes a first display region 110 to display time information at the time of signal detection in the horizontal direction (first direction) of the screen, and second display regions 101 to 103 to display a plurality of signal waveforms based on the signal detection in parallel in the vertical direction (second direction) of the screen.

The time information displayed in the first display region 110 is a time line including time indicators attached along a time axis 112 in the example of FIG. 4, but only a band-shaped axis may be used without indicating the time (number), or only the time (number) may be indicated without providing the axis. In addition, the time axis 112 may be displayed on the lower side of the display region 103 other than the display region 110 on the upper side of the screen, thereby indicating the time line.

A plurality of signal waveforms acquired from a plurality of sensors of the same type, or waveforms of a plurality of types of signals acquired from a plurality of types of sensor groups are displayed in the region 201A in synchronization with each other on the same time axis 112. For example, waveforms of a plurality of MEG signals obtained from the right side of the head of the subject are displayed in the display region 101, and waveforms of a plurality of MEG signals obtained from the left side of the head of the subject are displayed in the display region 102 to be parallel to each other. Waveforms of a plurality of EEG signals are displayed in parallel in the display region 103. These plural EEG signal waveforms are voltage signals measured between the respective electrodes. Each of these plural signal waveforms is displayed in association with an identification number or a channel number of the sensor from which the corresponding signal has been acquired.

When the measurement is started and measurement information from each sensor is collected, a signal waveform is displayed from a left end of each of the display regions 101 to 103 in the region 201A to the right direction with the lapse of time. A line 113 represents measurement time (present) and moves from the left to the right of the screen. When the signal waveform is displayed to a right end of the region 201A (a right end of the time axis 112), the signal waveform then gradually disappears from the left end to the right of the screen, a new signal waveform is sequentially displayed from the left to the right at the position where the waveform disappears, and the line 113 also moves from the left end to the right. At the same time, the lapse of time is displayed on the time axis 112 also in the display region 110 in the horizontal direction so as to correspond to the progress of the measurement. The measurement recording is continued until an end button 119 is pressed.

When a measurer (recorder) notices waveform disturbance, an amplitude singularity, or the like on a signal waveform during data recording, it is possible to mark a problematic point or a range on the signal waveform, which is a characteristic of the embodiment. Such a marking point or range can be designated by a pointer operation or a click operation using the mouse. The designated point (or range) is highlighted on the signal waveforms of the display regions 101 to 103, and a designation result is displayed along the time axis 112 in the display region 110 at a corresponding time position or time range. Marking information including the display on the time axis 112 is stored together with signal waveform data. The designated point corresponds to a certain time, and the designated range corresponds to a certain range including the certain time.

In the example of FIG. 4, a range including one or more channels is designated in the display region 103 at time t1, and time including the time t1 is highlighted by a mark 103a-1. An annotation 110a-1 indicating the designation result is displayed at a corresponding time position in the display region 110 in association with the display of the mark 103a-1. Another waveform position or the vicinity thereof is marked in the display region 103 at time t2, and a mark 103a-2 is highlighted at the position (time t2) or a region in the vicinity thereof (at least a time range or any one of the plurality of waveforms is instructed). At the same time, the annotation 110a-2 is displayed at a corresponding time position (time range) in the display region 110. Incidentally, the annotation indicates granting of relating information to certain data as a note. In the present embodiment, the annotation is displayed as a note based on at least designated time information, and is displayed as a note in combination with a position at which a waveform based on at least the time information is displayed. In addition, the annotation may be displayed as a note in combination with corresponding channel information in the case of displaying a plurality of channels.

The annotation 110a-1 added to the display region 110 at the time t1 includes, as an example, an annotation identification number and information indicating an attribute of a waveform. In this example, an icon representing the attribute of the waveform and text information "strong spike" are displayed together with an annotation number "1".

When the measurer designates another waveform point or a region in the vicinity thereof at the time t2, the mark 103a-2 is highlighted at the designated point. At the same time, an annotation number "2" is displayed at a corresponding time position in the display region 110. Further, a pop-up window 115 for attribute selection is displayed in the highlighted point. The pop-up window 115 has selection buttons 115a to select various attributes and an input box 115b to input a comment or additional information. Factors of waveform disturbance, such as "fast activity", "eye motion", "body motion", and "spike", are illustrated, as waveform attributes, in the selection buttons 115a. Since the measurer can confirm the state of the subject with the monitor window 170 in the region 201B of the screen, the measurer can appropriately select an attribute indicating the factor causing the waveform disturbance. For example, when a spike is generated in a waveform, it is possible to determine whether the spike is a spike indicating a symptom of epilepsy or a spike caused by a body motion (a sneeze or the like) of the subject.

The same operation is also performed at the time t1, and in FIG. 4, the selection button 115a of "spike" is selected in the pop-up window 115, and the annotation 110a-1 is displayed in the display region 110 as "strong spike" is input in the input box 115b. With such a display mode, it is possible to easily specify a point or range of interest of the signal waveform by visual recognition, and easily know basic information of the point of interest when displaying a large number of signal waveforms in synchronization with each other on the same time axis 112.

A part or the whole of the annotation 110a-1, for example, at least one of an attribute icon and a text annotation may be also displayed near the mark 103a-1 on the signal waveform of the display region 103. There may be a case where the addition of the annotation on the signal waveform hinders a check of a waveform shape, and thus, it is desirable to allow display or non-display to be selectable in the case of displaying the annotation on the signal waveforms of the display regions 101 to 103.

A counter box 118 displays a cumulative number of spike annotations. A counter value of the counter box 118 is incremented each time "spike" is selected, and the total number of spikes from the start of recording to the present (the line 113) can be known at a glance.

Figure 5:
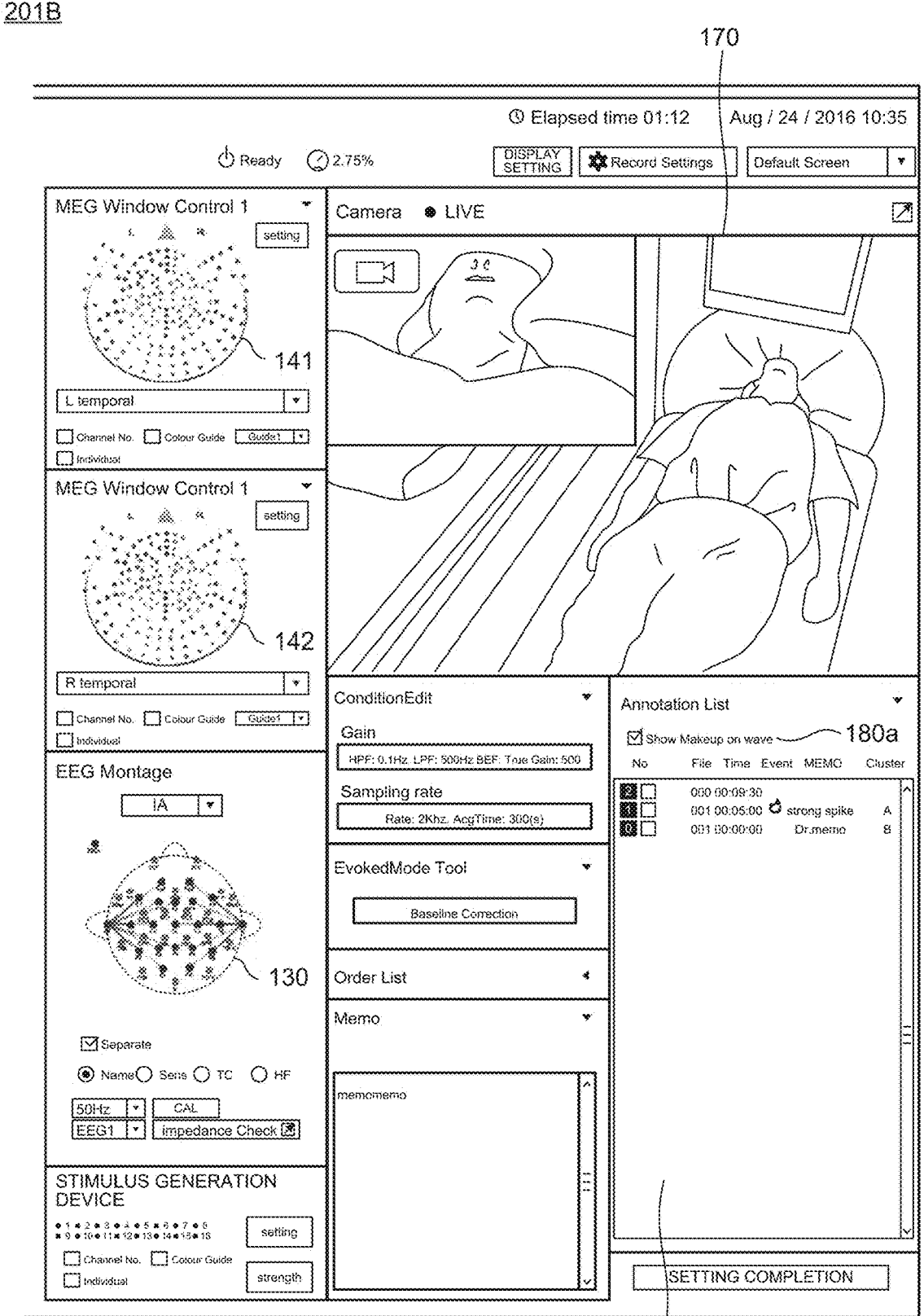
FIG. 5 is an enlarged view of a region on the right side of the measurement recording screen.

FIG. 5 is an enlarged view of the region 201B on the right side of FIG. 3, and illustrates a state at the same time (time of the line 113) as in FIG. 4. A live image of the state of the subject who is lying on the measurement table 4 with the head portion entering the measurement device 3 is displayed in a monitor window 170 of the region 201B. Distribution diagrams 141, 142, and 130 corresponding to the signal waveforms of the display regions 101, 102, and 103, respectively, and an annotation list 180 are displayed in the region 201B. The annotation list 180 is a list of annotations marked on the signal waveform of FIG. 4. Each time a position or a range on the signal waveform is specified in the display regions 101 to 103 and an annotation is given, corresponding information is sequentially added to the annotation list 180. The addition to the annotation list 180 and display of the annotation list 180 on the measurement recording screen are performed, for example, in descending order (new data is displayed on the top), but are not limited to this example. The annotation list 180 may be displayed in ascending order, but is displayed such that a correspondence relationship with the annotation displayed along the time axis 112 in the display region 110 can be known. Further, it is also possible to change the display order or perform sorting for each item.

In the example of FIG. 5, time information corresponding to an annotation number "1" and added annotation information are listed. An attribute icon representing "spike" and text "strong spike" are recorded as the annotation information. In addition, time information corresponding to an annotation number "2" is listed at the time when the mark 103a-1 is highlighted. Here, "annotation" may be considered as a set of an annotation number, time information, and annotation information, may be considered only as annotation information, or may be considered as a set of annotation information and an annotation number or time information.

In addition, a display/non-display selection box 180a is arranged near the annotation list 180. When non-display is selected in the selection box 180a, annotations other than the highlighted mark on the signal waveform are not displayed in the display regions 101 to 103, but the display of the annotation along the time axis 112 in the display region 110 is maintained. As a result, it is possible to recognize the annotation information without disturbing the visibility of the signal waveform.

Figure 6:
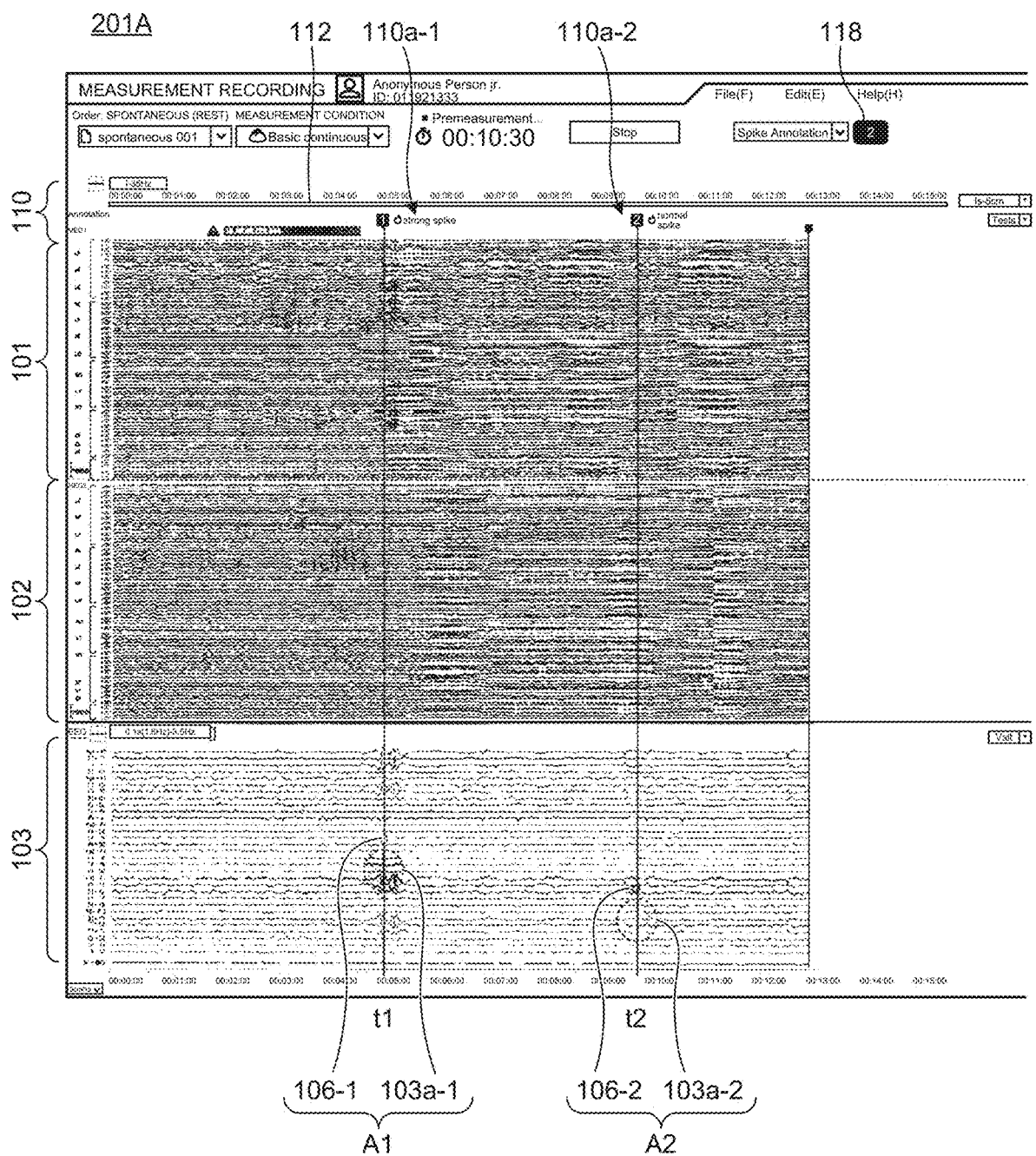
FIG. 6 is a view illustrating a screen immediately after input of annotation information.

FIG. 6 illustrates a screen immediately after "spike" of the pop-up window 115 is selected at the time t2 and text "normal spike" is input. When an "OK" button is selected in the pop-up window 115 illustrated in FIG. 4, the pop-up window 115 is closed, and the annotation 110a-2 is displayed at the corresponding time position in the display region 110 as illustrated in FIG. 6. The attribute icon representing "spike" and text information "normal spike" are displayed in association with the annotation number "2". At the same time, the value of the counter box 118 is incremented. In addition, an attribute icon 106-2 is displayed near the highlighted mark 103a-2. Although an attribute icon 106-1 is displayed also near the mark 103a-1 in this example, the display or non-display of the attribute icons 106-1 and 106-2 can be selected as described above. An annotation A1 including the mark 103a-1 and attribute icon 106-1 and an annotation A2 including the mark 103a-2 and the attribute icon 106-2 are also included in the annotation information.

FIG. 7 illustrates the annotation list 180. The annotation list 180 is updated as an annotation corresponding to the mark 103a-2 is added in the region 201A on the left side of the screen. A memo "normal spike" is added to the annotation number "2".

Hereinafter, each time a specific point or range on a signal waveform is designated in the region 201A during the measurement, the designated point is highlighted and annotation information is displayed along the time axis 112 in the display region 110 in the same manner. The annotation information is sequentially added to the annotation list 180 in the region 201B.

The display of the annotation number is not indispensable, and is not necessarily used in the annotation list 180 and the region 201A displaying the signal waveform. Arbitrary information can be used as identification information as long as the information enables identification of the added annotation. For example, an attribute icon, and an attribute character string ("strong spike" or the like) may be displayed in association with a time near the time axis 112. Further, a file number (a number displayed in an item "File" in FIG. 7) may also be displayed in the region 201A.

When an end button 119 (illustrated in FIG. 4) is selected (pressed) and the measurement is completed, the highlighted point designated in the display regions 101 to 103 is stored in association with the signal waveform. The annotation information displayed at the corresponding time position in the display region 110 is also stored in association with the annotation number and time. Related information such as the counter value of the counter box 118 and contents of the annotation list 180 is also stored. As these pieces of display information are stored, an analyst can easily recognize and analyze the problematic point even if the measurer and the analyst are different.

Figure 8:
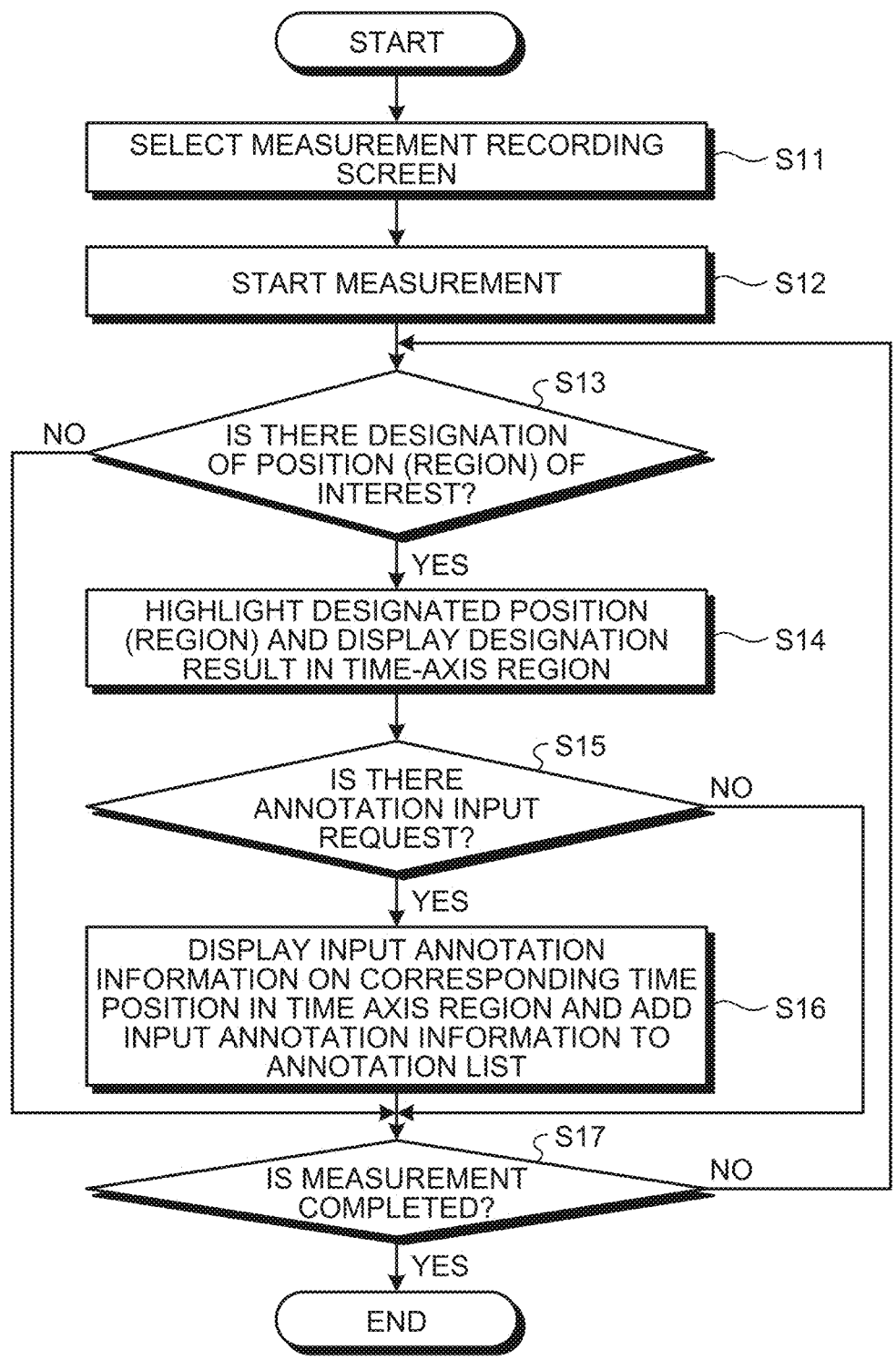
FIG. 8 is a flowchart illustrating an operation of the information processing apparatus at the time of measurement recording.

FIG. 8 is a flowchart of information display processing at a measurement recording stage performed by the information processing apparatus 50. When "measurement recording" has been selected on the start screen 204 illustrated in FIG. 2 (Step S11), the measurement is started and waveforms of a plurality of signals are displayed in synchronization with each other along the same time axis (Step S12). Here, the "plurality of signal waveforms" include both signal waveforms detected by a plurality of sensors of the same type and a plurality of signal waveforms detected by different types of sensors. The waveforms of the plurality of biological signals are constituted by waveforms of MEG signals obtained from a magnetic sensor group corresponding to the right side of the head of the subject, waveforms of MEG signals obtained from a magnetic sensor group corresponding to the left side of the head of the subject, and waveforms of EEG signals obtained from electrodes for the EEG measurement of the subject in this example, but the present invention is not limited thereto. Incidentally, a sensor can be arbitrarily selected from parts such as the parietal portion, frontal lobe, and temporal lobe regardless of the left or right sensor group. For example, when a sensor at the parietal portion is selected in "MEG Window Control 1" illustrated in FIG. 5 and the like, a sensor other than the sensor is selected in "MEG Window Control 2".

The information processing apparatus 50 determines whether a point or range of interest has been designated on the displayed signal waveform (Step S13). When the point or range of interest is designated (Step S13: Yes), the designated point is highlighted in the display region (display regions 101 to 103) of the signal waveform, and a designation result is displayed at a corresponding time position in the time-axis region (display region 110) (Step S14). The designation result includes information indicating the fact itself that the designation has been made or designated identification information. At the same time as, or before or after the display of the designation result in the time-axis region, whether there is an annotation input request is determined (Step S15). When there is the annotation input request (Step S15: Yes), the input annotation information is displayed at a corresponding time position in the time-axis region and is added to the annotation list (Step S16). Thereafter, whether a measurement end command is input is determined (Step S17). When the position (region) of interest is not designated (Step S13: No) or when there is no annotation input request (Step S15: No), the process jumps to Step S17 to make a determination of measurement end. Steps S13 to S16 are repeated until the measurement is completed (Step S17: Yes).

With this information display method, the measurement recording screen with high visibility of signal information is provided when collecting signals from a plurality of sensors.

<Operation During Analysis>

Figure 9:
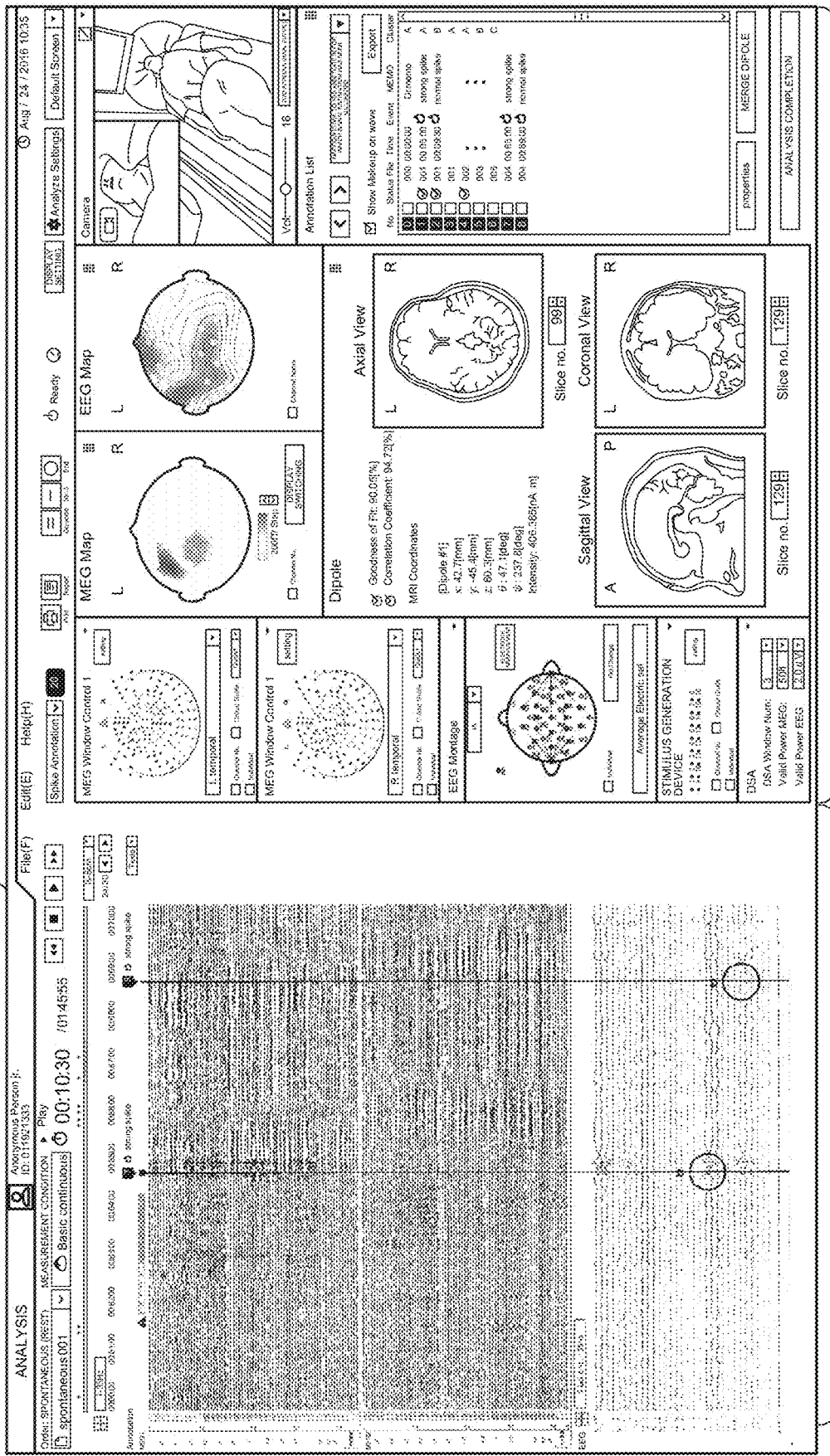
FIG. 9 is a view illustrating an example of an analysis screen.

FIG. 9 illustrates an example of a screen of the information processing apparatus 50 during analysis. An analysis screen is displayed by selecting the "analysis" button on the start screen 204 of FIG. 2. The "analysis" screen is displayed on the tab 111 on the screen. The analysis screen is a screen in which biological data indicating temporal changes of one or more biological signals (in this example, the MEG signals obtained from the magnetic sensor group corresponding to the right side of the head of the subject, the MEG signals obtained from the magnetic sensor group corresponding to the left side of the head of the subject, and the EEG signals obtained from the electrodes for the EEG measurement of the subject) of the subject by the measurement in association with the annotation input to the biological data during the measurement. The information processing apparatus 50 according to the present embodiment has a function of performing control to display this analysis screen on a display unit (the display device 28 described later). In the example of FIG. 9, the analysis screen has a region 202A to display waveforms (corresponding to the biological data) indicating temporal changes of three recorded biological signals together with annotations and a region 202B to display analysis information. The region 202A to display the recorded signal waveform and annotation information is arranged on the left side of the screen as viewed from the measurer and the region 202B to display the analysis is arranged on the right side as viewed from the measurer. This allows favorable work efficiency in confirming or determining an analysis result in the region 202B by operating a mouse or the like while checking or selecting the signal waveform in the region 202A during the analysis.

In this example, the waveforms of the MEG signals of the second display regions 101 and 102 are displayed at the upper side of a waveform screen of the EEG signal in the second display region 103 of the region 202A. In addition, MEG distribution diagrams 141 and 142 are displayed in a screen region closer to the region 202A at the upper side of the screen in the region 202B on the right side of the region 202A, and an EEG distribution diagram 130 is displayed at the lower side of the MEG distribution diagrams 141 and 142. Thus, the analyst performs gaze movement in the order of "EEG signal waveform" in the second display region 103→"MEG signal waveform" in the second display regions 101 and 102→the MEG distribution diagrams 141 and 142→the EEG distribution diagram 130 (in this case, in the clockwise direction). Thus, the gaze movement of the analyst (or the measurer) becomes efficient, and as a result, the analysis work efficiency can be improved. Incidentally, the description has been given by exemplifying the clockwise direction as above, but the present invention is not limited to this example.

Figure 10:
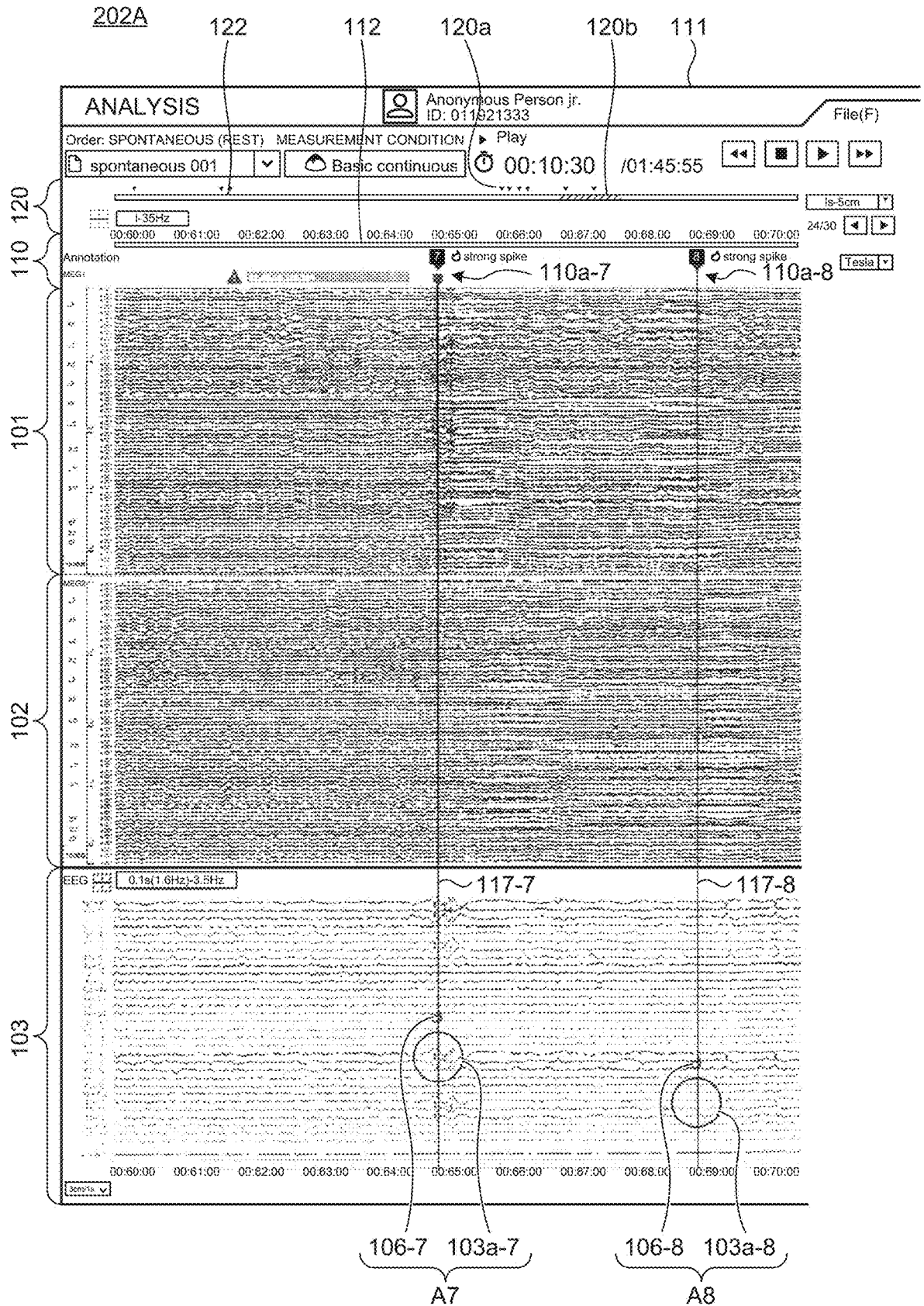
FIG. 10 is an enlarged view of a region on the left side of the analysis screen.

FIG. 10 is an enlarged view of the region 202A on the left side of FIG. 9. The region 202A includes a display region 110 and a display region 120 to display time information at the time of the measurement in the horizontal direction (first direction) of the screen, and display regions 101 to 103 to display recorded signal waveforms side by side in the vertical direction (second direction) of the screen for each type.

In the display region 110, a time axis 112 indicating the lapse of time during recording and annotations 110a-7 and 110a-8 added along the time axis 112 are displayed. In the display region 120, a time axis 122 indicating the total recording time is displayed. A pointer mark 120a indicating a time position at which an annotation is added and a time zone 120b indicating a time zone in which signal waveforms currently being displayed in the display regions 101 to 103 are recorded are displayed along the time axis 122. With this display, the analyst can intuitively know at which stage during measurement recording a signal waveform currently being analyzed is acquired.

After opening the analysis screen, the analyst can display a signal waveform in a desired time zone in the display regions 101 to 103 by, for example, dragging the time zone 120b on a bar of the time axis 122. Alternatively, a desired annotation can be selected from the annotation list 180 to display signal waveforms before and after the annotation is included in the display regions 101 to 103 as will be described later.

Annotations A7 and A8 added to the signal waveforms during recording are displayed in the display regions 101 to 103. Marks 103a-7 and 103a-8 are highlighted, and attribute icons 106-7 and 106-8 each of which corresponds to the vicinity of each of the marks 103a-7 and 103a-8 are displayed. In addition, vertical lines 117-7 and 117-8 indicating time positions of the marks 103a-7 and 103a-8 are displayed. With the display of the lines 117-7 and 117-8, for example, when an annotation is added in association with designation of a predetermined point of the display region 103, it is possible to visually recognize a result of the designation easily even in the display regions 102 and 101, which are different types of signal display areas. The lines 117-7 and 117-8 can be included in the annotation information in terms of facilitating the visual recognition of the annotation information, and may be referred to as "annotation lines". As the lines 117-7 and 117-8 are selected, the signal waveform is displayed in an enlarged manner including a certain period of time before and after the time of selection. This processing will be described later.

Figure 11:
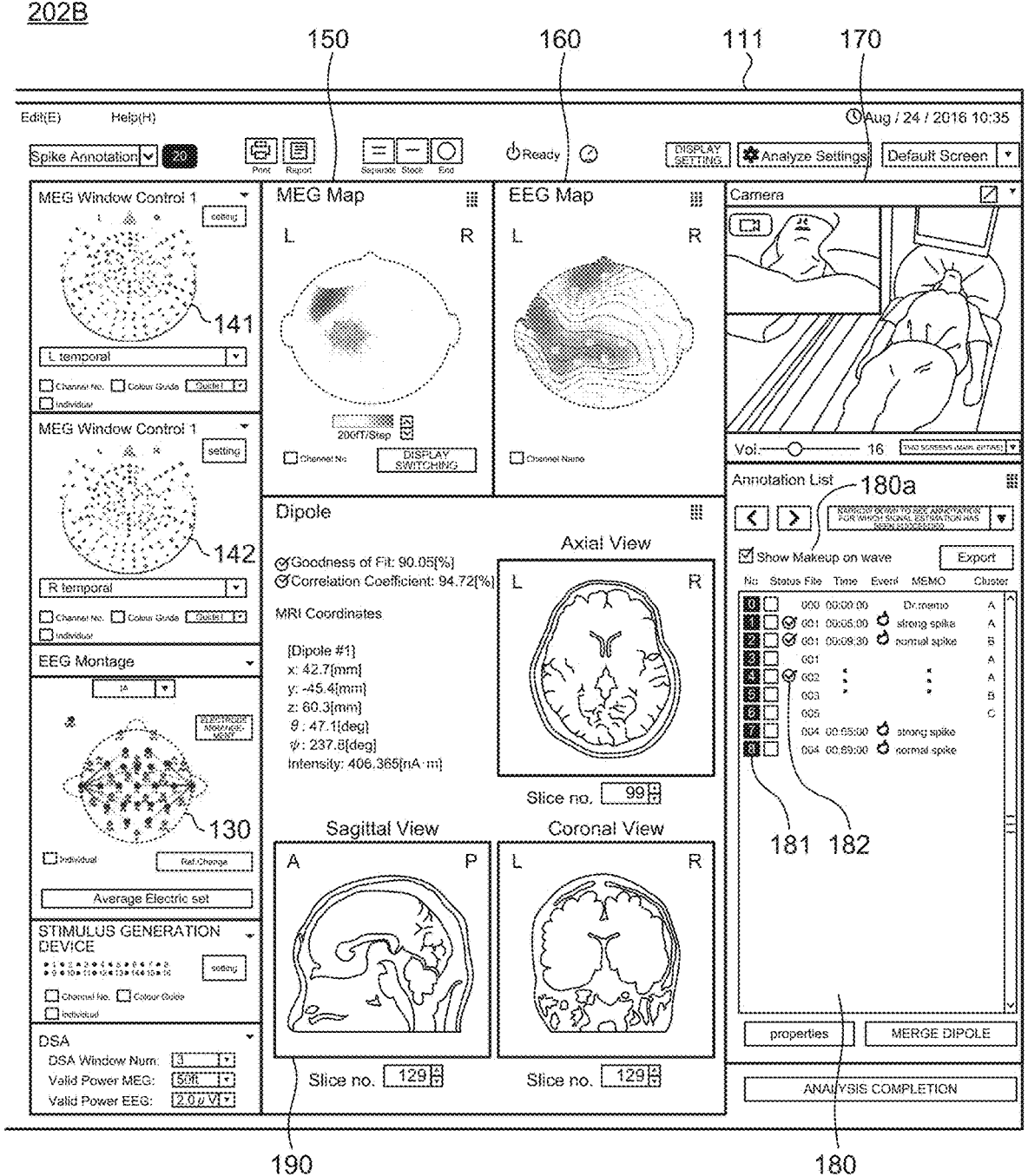
FIG. 11 is an enlarged view of a region on the right side of the analysis screen.

FIG. 11 is an enlarged view of the region 202B on the right side at the same time as that in FIG. 10. The MEG distribution diagrams 141 and 142 corresponding to the signal waveforms displayed in the display regions 101 and 102 and the EEG distribution diagram 130 corresponding to the signal waveform displayed in the display region 103 are displayed. In addition, an isomagnetic map 150 of a magneto-encephalograph (MEG), a map area 160 of an electro-encephalograph (EEG), and a display window 190 of a tomographic image of the brain of the subject, acquired by magnetic resonance imaging (MRI), are displayed. In the isomagnetic map 150, a spouting region and a subduction region of a magnetic field are displayed in a color-coded manner, and a direction in which the current flows is visually known. The isomagnetic map 150 and the map area 160 are information obtained after the completion of the measurement, and the tomographic image of MRI is information obtained separately in an examination.

An image of the subject during the measurement is displayed in the monitor window 170 in synchronization with the time at which the signal waveforms of the display regions 101 to 103 are acquired. The analyst can analyze the signal waveform while confirming the state of the subject by viewing the monitor window 170.

All the annotations added in the measurement recording are listed in the annotation list 180. Annotation information (an attribute icon, text input information, or the like) added in association with an annotation number 181 is described in the annotation list 180. For example, the added annotations are displayed in ascending order (such that old data is on the top) in the annotation list 180 of the analysis screen, but the present invention is not limited thereto. The use of the annotation number is not indispensable similarly to the measurement recording screen, and the annotation can be also identified by a combination of time, a file name, an attribute, and the like. In addition, it is also possible to change the display order of the annotations included in the annotation list 180 and perform sorting for each item. By clicking a desired annotation number 181 or row, it is possible to display a signal waveform in a predetermined time zone including a time position to which an annotation thereof is added in the display regions 101 to 103 of FIG. 10.

An estimation completion mark 182 (illustrated in FIG. 11) is displayed in an annotation for which the analyst has confirmed a signal waveform of an annotation part and finally estimated a signal source, which is different from the measurement recording screen.

When non-display is designated in the selection box 180a configured to select display/non-display of the annotation, the attribute icons 106-7 and 106-8 in the display region 103 of FIG. 10 disappear. The non-display of the highlighted marks 103a-7 and 103a-8 may be selected by the display/non-display selection box 180a.

Figure 12:
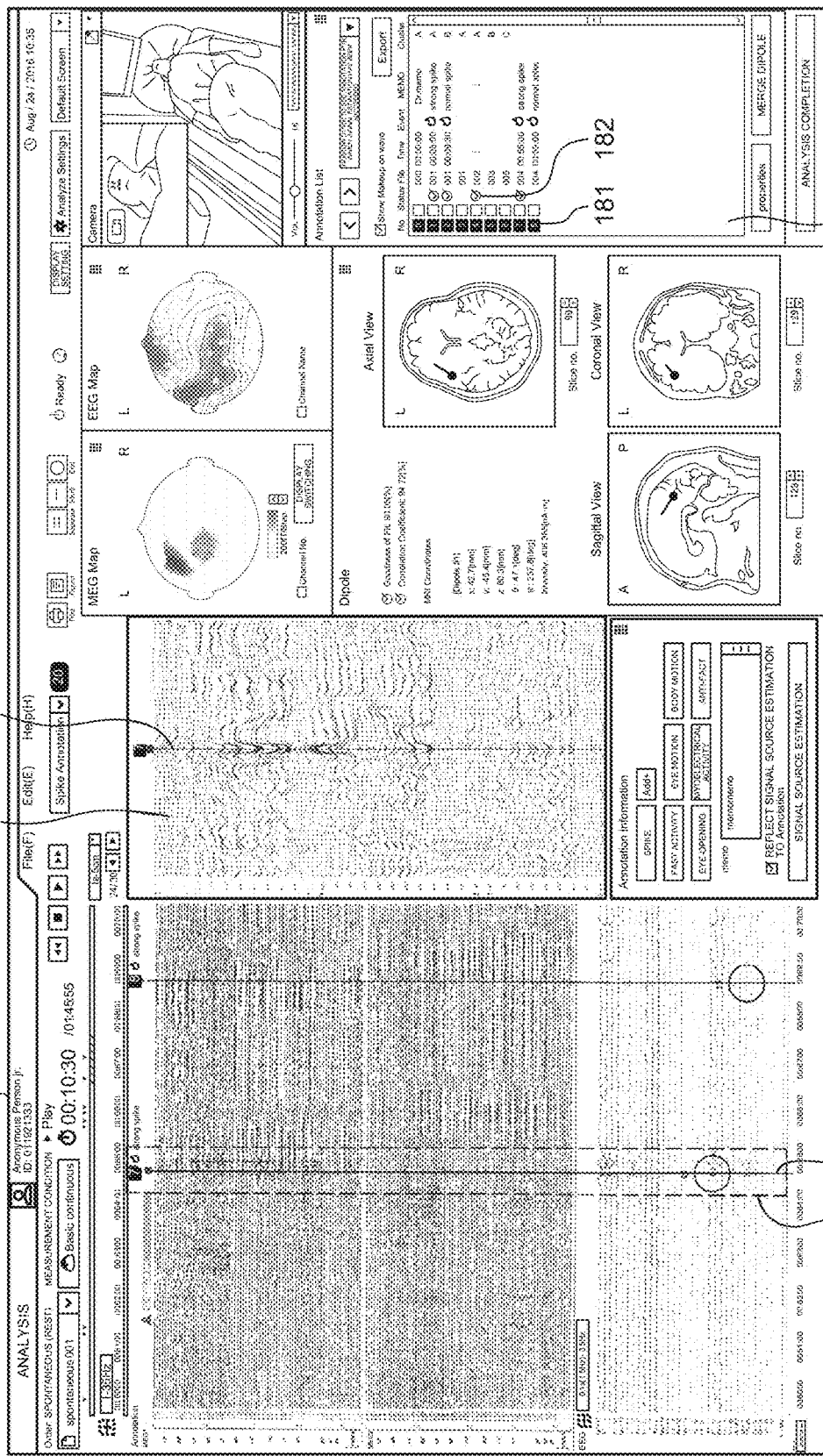
FIG. 12 is a view illustrating a screen immediately after a specific annotation line is selected on the analysis screen.

FIG. 12 is an overall view of a screen immediately after the line 117-7 is selected (for example, double-clicked) on the analysis screen of FIG. 10. When the analyst focuses on the annotation A7 and selects (for example, double-clicks) the line 117-7 in order to analyze the waveform in this region, a signal waveform near the highlighted signal waveform is displayed in an enlarged display region 200 in an enlarged manner. The signal waveform is displayed in an enlarged manner together with a line 217-7 indicating the time position over a certain time range indicated by a region 114.

Figure 13:
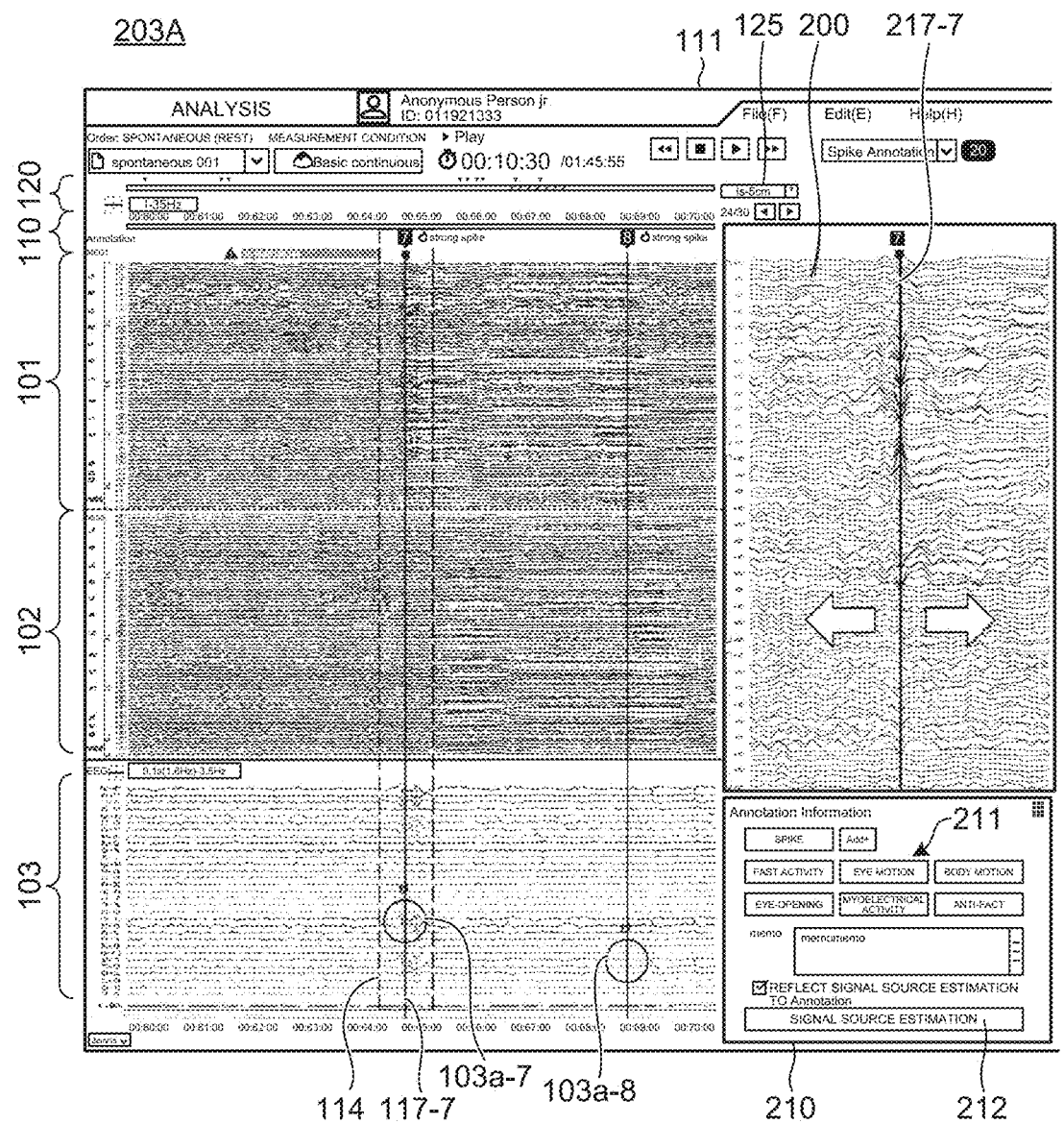
FIG. 13 is an enlarged view of a region on the left side of the screen of FIG. 12.

FIG. 13 is an enlarged view of a region 203A (a display region of a signal waveform) on the left side of FIG. 12. The analyst can reconfirm validity of a mark added during recording or check a waveform portion which has not been checked during measurement recording by displaying the signal waveform in an enlarged manner in the enlarged display region 200. For example, it is possible to specify or change an exact point of the waveform that causes a problem by dragging the line 217-7 to the left or right. A mark 103a highlighted in the display region 103 and/or an attribute icon 106 may be reflected in the enlarged display region 200. However, it is desirable to enable selection of display or non-display when displaying the highlighted mark 103a or the attribute icon 106 in the enlarged display region 200 since a case in which the display thereof may hinder confirmation at the time of accurately determining a singularity of amplitude is considered.

It is also possible to designate a type of a signal waveform to be displayed in the enlarged display region 200 and a channel range. For example, the analyst moves the gaze from the mark 103a-7 highlighted in the display region 103 to the upper part of the screen and confirms whether there is a singularity of amplitude in the waveform of the display region 101 or 102 of the MEG waveform. In this case, it is possible to display the MEG waveform associated with the mark 103a-7 in an enlarged manner in the enlarged display region 200 by inputting a target channel region in the display region 101 or 102 in a box 125.

A confirmation window 210 is displayed on the lower side of the screen of the enlarged display region 200. The confirmation window 210 includes an attribute button 211 of a signal waveform and an estimation button 212 of a signal source. The attribute button 211 corresponds to the attribute information included in the pop-up window 115 of the measurement recording screen, and it is possible to select a correct attribute by selecting the attribute button 211 when the attribute added during recording is erroneous. When the selection of a correct position and/or attribute of a signal waveform is confirmed, it is possible to reflect estimation of a signal source to an annotation by clicking the estimation button 212. That is, the information processing apparatus 50 according to the present embodiment has a function of estimating the signal source corresponding to the annotation selected from the analysis screen. The estimated signal source is superimposed and displayed on the tomographic image corresponding to the estimated signal source among a plurality of MRI tomographic images as will be described later.

Figure 14:
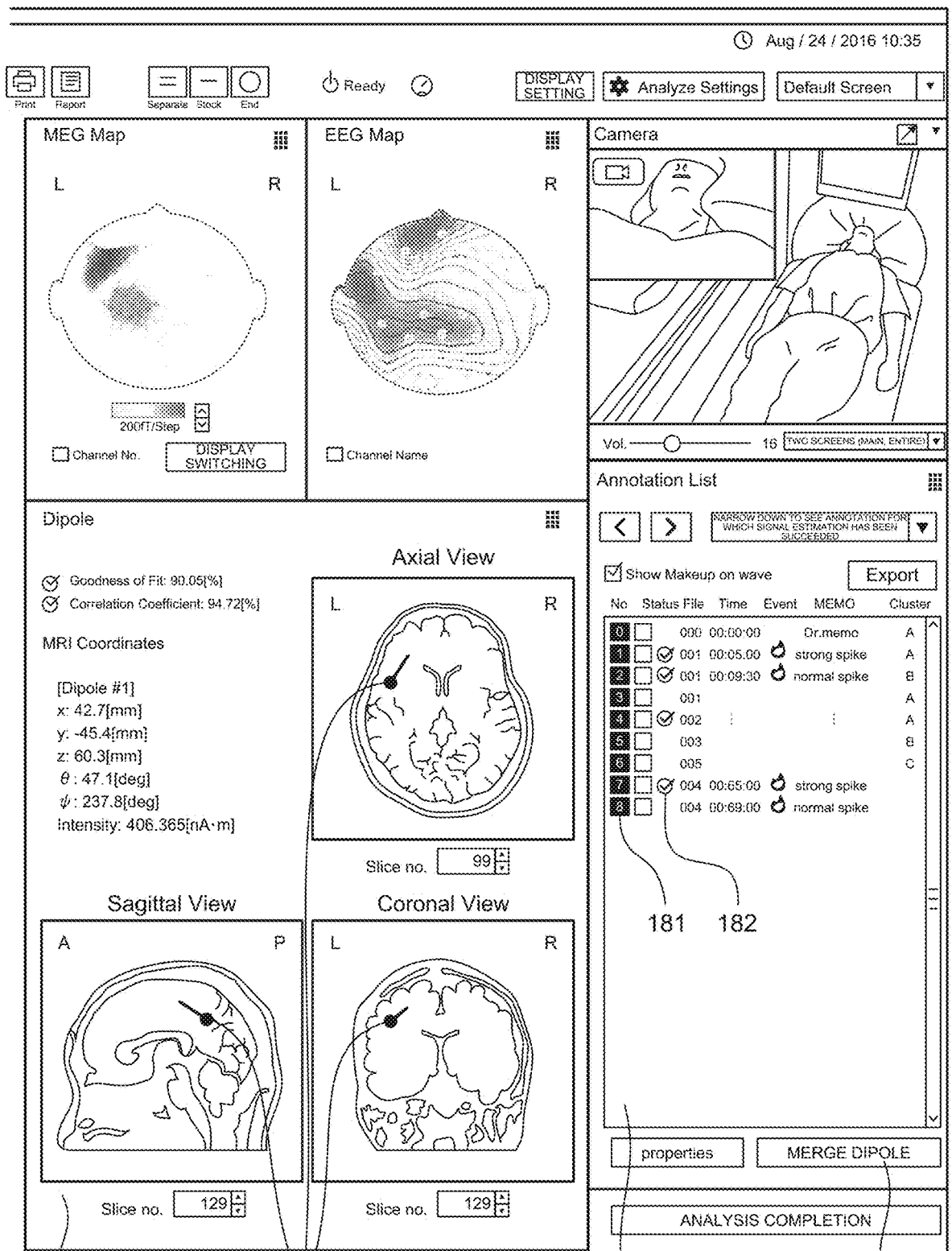
FIG. 14 is an enlarged view of a region on the right side of the screen of FIG. 12.

FIG. 14 is an enlarged view of a region 203B on the right side of FIG. 12. When a signal waveform position and/or an attribute is confirmed for a desired annotation and the signal source estimation button 212 is selected in FIG. 13, the estimation completion mark 182 is added to the corresponding annotation (in this example, the annotation number "7") in the annotation list 180. Further, a dipole estimation result 190a is displayed in the MRI tomographic image of the display window 190.

There are two methods as a method of updating the annotation list 180 when the analyst changes the mark position highlighted in the display regions 101 to 103 and/or the contents of the annotation. That is, the method of reflecting only latest update information updated by the analyst on the annotation list 180 and the method of adding the latest update information as new annotation information while maintaining the annotation information at the time of measurement recording. When adopting the latter method, for example, a branch number from an annotation number at the time of recording can be assigned as annotation identification information. In this case, the new annotation information may be added to the display region 110 as well, and the added annotation information may be displayed using a different color along the time axis.

Figure 15:
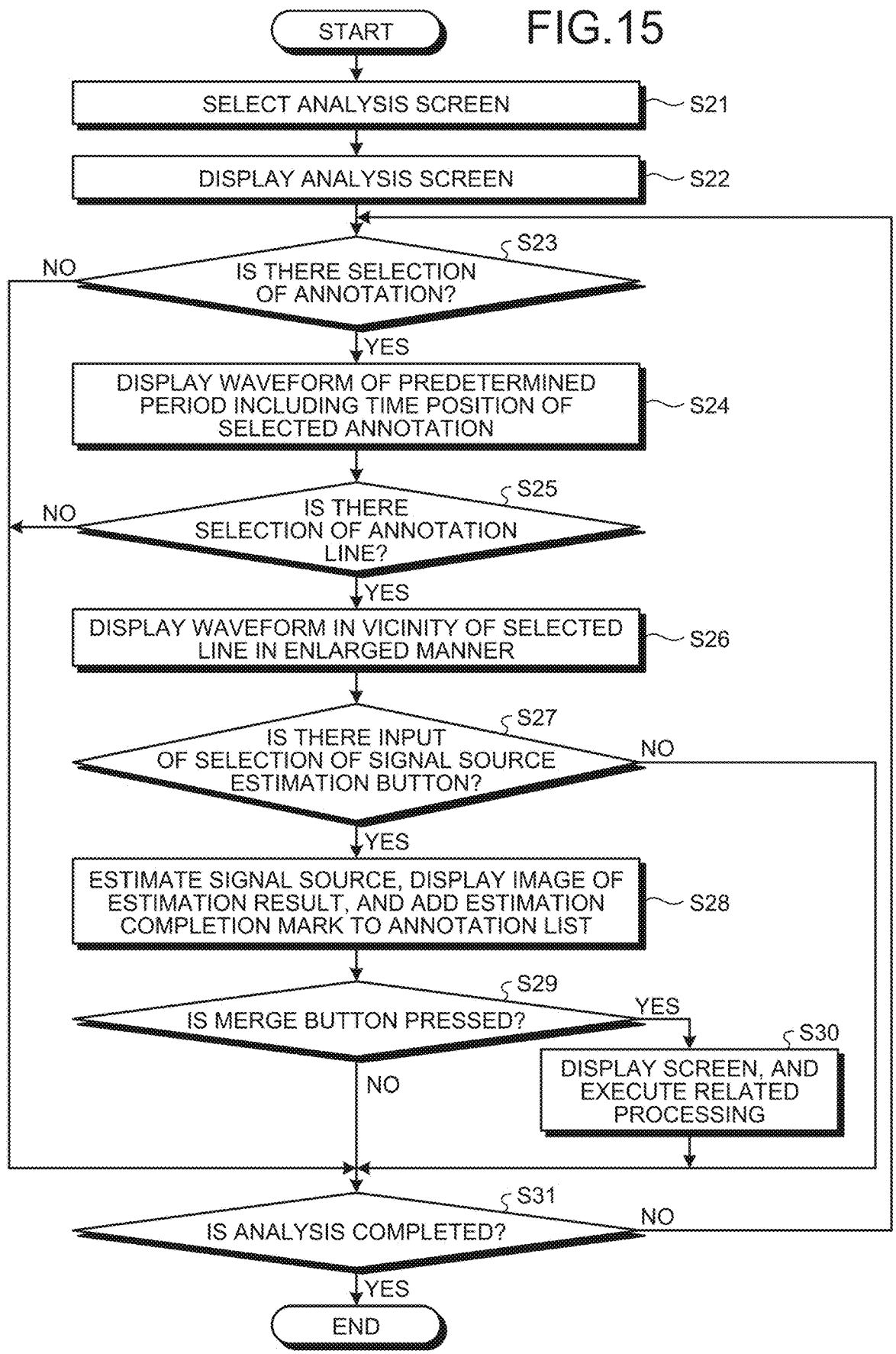
FIG. 15 is a flowchart illustrating an operation of the information processing apparatus at the time of analysis.

FIG. 15 is a flowchart of information display processing at an analysis stage performed by the information processing apparatus 50. When "analysis" is selected on the start screen 204 (see FIG. 2) (Step S21), the analysis is started and the analysis screen is displayed (Step S22). The initial analysis screen may be a blank screen on which no signal waveform is displayed, or may be a signal waveform in a predetermined time range at the beginning or the end of recording. When the analysis screen is displayed, whether a specific annotation has been selected is determined (Step S23). The selection of the annotation may be selection of a specific annotation number or row in the annotation list 180 or may be designation of a time position by operating the time zone 120b on the time axis 122 of the display region 120. When the annotation is selected (Step S23: Yes), a signal wavelength corresponding to a predetermined time including the time position of the selected annotation is displayed (Step S24).

Whether the line 117 indicating the time position of the highlighted mark has been selected on the displayed scene is determined (Step S25). When the line 117 is selected (Step S25: Yes), a signal waveform in a certain time range including the selected line is displayed in an enlarged manner (Step S26). The enlarged display is not necessarily limited to the signal waveform near the highlighted mark, and different types of signal waveforms at the same time position may be enlarged and displayed. For example, when an EEG signal waveform is marked with highlighted, an MEG signal waveform at the same time position may be enlarged and displayed. In addition, a signal waveform, acquired in a certain range of channels including a channel from which a marked signal waveform has been acquired, may be enlarged and displayed instead of enlarging and displaying signal waveforms of all the channels. In this case, a type of a signal waveform to be desirably enlarged and displayed and/or the presence or absence of designation input of a channel range may be determined.

Next, whether the signal source estimation button 212 has been pressed is determined (Step S27). When the signal source estimation button 212 is pressed (Step S27: Yes), calculation for signal source estimation is performed. An estimation result is displayed on an MRI tomographic screen, and the estimation completion mark 182 is added to the annotation list 180 (Step S28). Then, when receiving the press of a merge button 300 arranged below the annotation list 180 (Step S29: Yes), the information processing apparatus 50 displays a screen 400 to be described later and performs processing relating to the screen 400 (Step S30). Specific contents of Step S29 and Step S30 will be described later. When the press of the merge button 300 has not been received (Step S29: No), or after Step S30, whether an analysis end command has been input is determined (Step S31). The processing jumps to Step S31 to make a determination of analysis end when there is no selection of the annotation (Step S23: No), when there is no selection of the annotation line for enlarged display (Step S25: No), and when there is no input of press of the signal source estimation button 212 (Step S27: No). Steps S23 to S30 are repeated until the analysis end command is input (Step S31: Yes).

Whether the annotation has been changed may be determined between Steps S26 and S27. When the annotation has been changed, such a change is reflected in the annotation list 180, and the processing transitions to the determination in Step S27.

With the above-described display processing operation, information display excellent in visibility and operability is realized.

Figure 16:
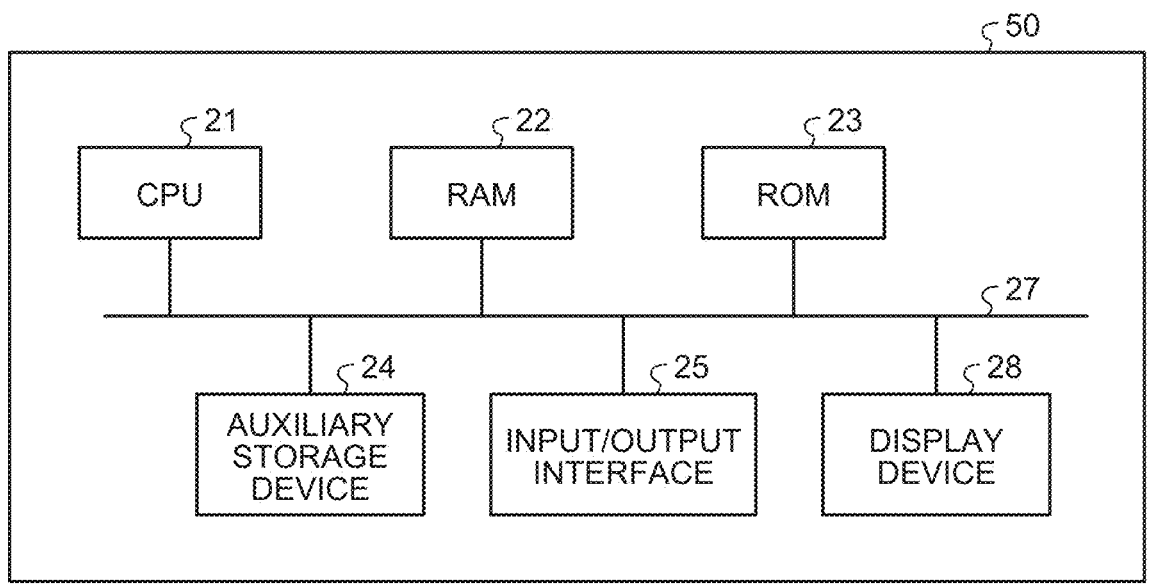
FIG. 16 is a hardware configuration diagram of the information processing apparatus.

FIG. 16 is a hardware configuration diagram of the information processing apparatus 50. The information processing apparatus 50 includes a central processing unit (CPU) 21, a random access memory (RAM) 22, a read only memory (ROM) 23, an auxiliary storage device 24, an input/output interface 25, and the display device 28, and these units are connected to each other via a bus 27.

The CPU 21 controls the overall operation of the information processing apparatus 50 and performs various types of information processing. The CPU 21 also executes an information display program stored in the ROM 23 or the auxiliary storage device 24 to control display operations of the measurement recording screen and the analysis screen. The RAM 22 is used as a work area of the CPU 21 and may include a non-volatile RAM that stores main control parameters and information. The ROM 23 stores a basic input/output program and the like. The information display program of the present invention may also be stored in the ROM 23. The auxiliary storage device 24 is a storage device such as a solid state drive (SSD), and a hard disk drive (HDD), and stores, for example, a control program to control the operation of the information processing apparatus 50, various data necessary for the operation of the information processing apparatus 50, files, and the like. The input/output interface 25 includes both a user interface such as a touch panel, a keyboard, a display screen, and an operation button, and a communication interface that takes in information from various sensors or the server 40 and outputs analysis information to other electronic devices. The display device 28 is a monitor display to display various types of information. In the display device 28, the measurement recording screen and the analysis screen are displayed, and the screen is updated according to an input/output operation performed via the input/output interface 25.

Figure 17:
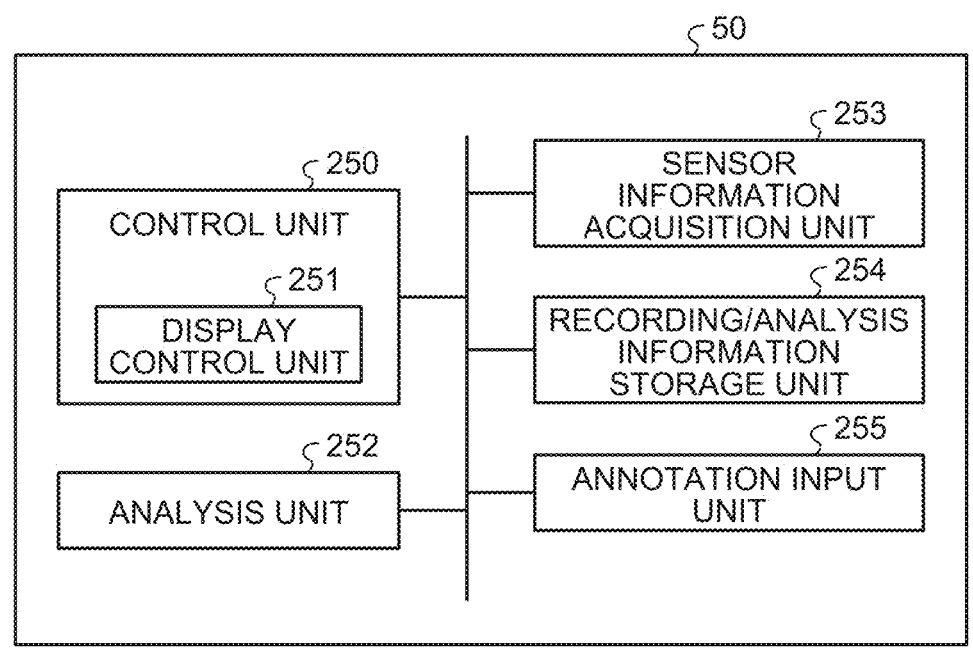
FIG. 17 is a functional block diagram of the information processing apparatus.

FIG. 17 is a functional block diagram of the information processing apparatus 50. The information processing apparatus 50 includes a control unit 250, an analysis unit 252, a sensor information acquisition unit 253, a recording/analysis information storage unit 254, and an annotation input unit 255. The control unit 250 includes a display control unit 251 that controls screen display of the information processing apparatus 50.

The sensor information acquisition unit 253 acquires sensor information from the measurement device 3 or the server 40. The annotation input unit 255 inputs the annotation information added to the sensor information. The analysis unit 252 analyzes the collected sensor information. The analysis of sensor information includes analysis of a signal waveform, analysis of a singularity of amplitude, and analysis of a brain magnetic field including a current dipole direction. That is, the analysis unit 252 has a function (a function of an estimation unit) that estimates a signal source corresponding to an annotation selected from the analysis screen in this example. The display control unit 251 controls screen display during the measurement recording and analysis of the sensor information using the method described with reference to FIGS. 2 to 17. The recording/analysis information storage unit 254 stores measurement data and an analysis result. When an annotation is added to a signal waveform during the measurement recording, the annotation is also stored in association with time information at which the signal waveform is acquired. A function of the control unit 250 including the display control unit 251 is realized as the CPU 21 of FIG. 16 expands a program stored in the ROM 23 or the like on the RAM 22 and executes the program. The function of the analysis unit 252 is also realized as the CPU 21 expands a program stored in the ROM 23 or the like on the RAM 22 and executes the program. Incidentally, the present invention is not limited thereto, and may be provided in a mode, for example, in which at least a part of the functions of the control unit 250 and the analysis unit 252 is realized by a dedicated hardware circuit (semiconductor integrated circuit or the like). Functions of the sensor information acquisition unit 253 and the annotation input unit 255 are realized by the input/output interface 25. A function of the recording/analysis information storage unit 254 is realized by the ROM 23 or the auxiliary storage device 24.

Figure 18:
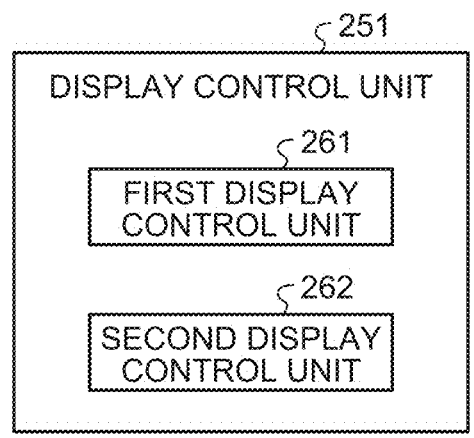
FIG. 18 is a diagram illustrating exemplary functions of a display control unit.

FIG. 18 is a diagram illustrating exemplary functions of the display control unit 251. As illustrated in FIG. 18, the display control unit 251 includes a first display control unit 261 and a second display control unit 262. In FIG. 18, only the functions relating to the present invention are illustrated, but functions of the display control unit 251 are not limited to these functions, and also have the above-described other functions.

The first display control unit 261 performs control to display the above-described analysis screen on the display device 28.

When signal sources are sequentially estimated by the analysis of the analysis unit 252 and the press of the merge button 300 arranged below the annotation list 180 is received as described above, the second display control unit 262 performs control so as to display a signal source corresponding to a part of biological data indicating a temporal change of a biological signal in a superimposed manner on a plurality of biological tomographic images sliced in a predetermined direction, and to initially display, in a display region, a biological tomographic image on which a predetermined signal source is superimposed among the plurality of sliced biological tomographic images. Herein, the predetermined signal source is a signal source that meets a predetermined condition. In this example, the predetermined condition is the number of signal sources, but the present invention is not limited thereto. In the present embodiment, the predetermined condition is the largest number of signal sources among the numbers of signal sources on the respective sliced biological tomographic images. The second display control unit 262 initially displays a biological tomographic image having the largest number of signal sources near a central portion of the display region although specific contents will be described later. Then, the second display control unit 262 arranges and displays other biological tomographic images such that the biological tomographic images are aligned in the order of layers laterally from the biological tomographic image near the central portion. In addition, the second display control unit 262 can also display a biological tomographic image on which no signal source is superimposed, or it is also possible to set the biological tomographic image on which no signal source is superimposed not to be displayed. Hereinafter, the specific contents will be described.

When receiving the press of the merge button 300 arranged below the annotation list 180 illustrated in FIG. 14, the second display control unit 262 performs control to display the screen 400 illustrated in FIG. 19 on the display device 28 in the present embodiment. The screen 400 includes a region 401A in which the plurality of biological tomographic images are displayed side by side in the lateral direction, and a region 401B in which a tomographic position of a biological tomographic image selected from the region 401A is displayed.

The region 401A is constituted by a display region 410A to display a tomographic image from the top (sometimes referred to as a "slice image A" in the following description), a display region 410B to display the tomographic image from a side direction (sometimes referred to as a "slice image B" in the following description), and a display region 410C to display the tomographic image from a back direction (sometimes referred to as a "slice image C" in the following description). In the following description, the slice images A, B, and C will be sometimes simply referred to as a "slice image" when not distinguished from each other. Incidentally, the vertical alignment direction of the tomographic images in the region 401A is not limited to the mode of the present embodiment.

Figure 20:
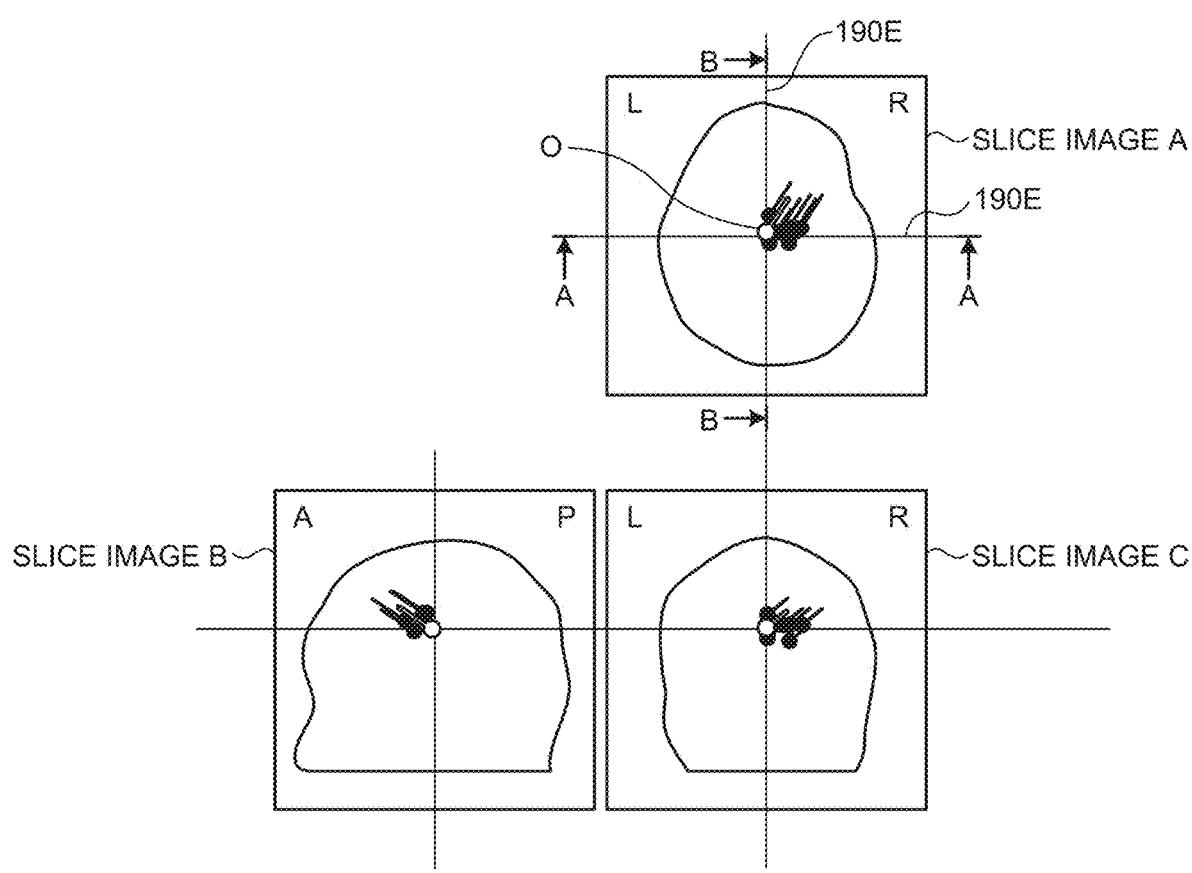
FIG. 20 is a view for describing a relationship among three slice images corresponding to three-dimensional directions.

Here, a relationship among the slice image A, the slice image B, and the slice image C corresponding to the three-dimensional directions will be described with reference to FIG. 20. In FIG. 20, positions of the slice images A to C are linked in the three-dimensional directions. Reference lines 190E are displayed so as to straddle the respective slice images, and intersections O of the respective reference lines 190E indicate slice positions of the respective slice images. In this example, the slice image C is a cross-sectional view of a cross section of the slice image A cut along the reference line 190E of the horizontal direction (lateral direction) as viewed from a direction A illustrated in FIG. 20. In addition, the slice image B is a cross-sectional view of a cross section of the slice image A cut along the reference line 190E of the vertical direction as viewed from a direction B illustrated in FIG. 20. In the following description, a viewpoint corresponding to the slice image A will be referred to as "Axial View", a viewpoint corresponding to the slice image B will be referred to as "Sagittal View", and a viewpoint corresponding to the slice image C will be referred to as "Coronal View".

That is, in this example, a biological tomographic image includes a first tomographic image (for example, the slice image A) that is a cross section in the first direction, a second tomographic image (for example, the slice image B) that is a cross section in the second direction orthogonal to the first direction, and a third tomographic image (for example, the slice image C) that is a cross section in a third direction orthogonal to the first direction and the second direction.

The description will be continued returning to FIG. 19. The second display control unit 262 performs control to display information indicating the number of signal sources to be superimposed together with a corresponding biological tomographic image. For each slice image, information 440A indicating a slice number indicating at which position the image has been sliced, and information 440B indicating the number of signal sources to be superimposed on the slice image (the number of dipole estimation results) are displayed in each of the display regions 410A to 410C.

The region 401B includes a display region 420A corresponding to the display region 410A, a display region 420B corresponding to the display region 410B, and a display region 420C corresponding to the display region 410C.

In the display region 420A, any position in a tomographic image viewed from each of the side (an image on the left side of the display region 420A) and the back (an image on the right side of the display region 420A) at which the slice image A displayed in the display region 410A has been sliced is displayed, and a tomographic position line 450 indicating such a tomographic position is displayed in a superimposed manner. The respective adjacent tomographic position lines 450 of a slice position A as viewed from the side and a slice position B as viewed from the back match in position in the vertical direction of the drawing. In addition, slice numbers corresponding to the respective tomographic position lines 450 are associated with the slice image A displayed in the display region 410A. For example, slice numbers 01 to 15 are assigned from the bottom to the top of the display region 420A.

Similarly, in the display region 420B, any position in a tomographic position viewed from each of the top (an image on the left side of the display region 420B) and the back (an image on the right side of the display region 420B) at which the slice image B displayed in the display region 410B has been sliced is displayed, and a tomographic position line 450 indicating such a tomographic position is displayed in a superimposed manner. The tomographic position lines 450 of a slice position C as viewed from the top and a slice position D as viewed from the back match in position in the lateral direction of the drawing. In addition, slice numbers corresponding to the respective tomographic position lines 450 are associated with the slice image B displayed in the display region 410B. For example, slice numbers 01 to 14 are assigned from the left to the right of the display region 420B.

Similarly, in the display region 420C, any position in a tomographic position viewed from each of the top (an image on the left side of the display region 420C) and the side (an image on the right side of the display region 420C) at which the slice image C displayed in the display region 410C has been sliced is displayed, and a tomographic position line 450 indicating such a tomographic position is displayed in a superimposed manner. The tomographic position lines 450 of a slice position E as viewed from the top match in position from the top to the bottom, and the tomographic position lines 450 of a slice position F viewed from the side match in position from the left to the right. In addition, slice numbers corresponding to the respective tomographic position lines 450 are associated with the slice image A displayed in the display region 410C. For example, slice numbers 01 to 15 are assigned from the top to the bottom of the display region 420C (in the case of the top tomographic image on the left side) or from the left to the right (in the case of the side tomographic image on the right side).

That is, the second display control unit 262 of the present embodiment performs control to display the information indicating the tomographic position of the biological tomographic image displayed in the region 401A (display region). In this example, the second display control unit 262 performs control to display the information indicating the tomographic position of the biological tomographic image selected from the plurality of biological tomographic images (slice images). Incidentally, each of the above-described tomographic position lines 450 and the above-described information 440A indicating the slice number are stored in the storage device (the auxiliary storage device 24 or the like) in association with each other.

In this example, a slice image having the largest number of dipole estimation results to be superimposed and displayed is arranged at the center among the slice images displayed in the respective display regions 410A to 410C. Then, the other slice images are arranged so as to be aligned in the order of slice numbers (in the order of layers) laterally from the center slice image. For example, a slice image with a slice number 10 is arranged at the center in the display region 410A, and slice numbers 11, 12, and 13 (only some thereof) are arranged in this order on the right side thereof. Further, slice numbers 9, 8, and 7 (only some thereof) are arranged in this order on the left side of the slice number 10. In addition, a slice image with a slice number 10 is arranged at the center in the display region 410B, and slice numbers 11, 12, and 13 (only some thereof) are arranged in this order on the right side thereof. Further, slice numbers 9, 8, and 7 (only some thereof) are arranged in this order on the left side of the slice number 10. Further, a slice image with a slice number 7 is arranged at the center in the display region 410C, and slice numbers 8, 9, and 10 (only some thereof) are arranged in this order on the right side thereof. Further, slice numbers 6, 5, and 4 (only some thereof) are arranged in this order on the left side of the slice number 7. Here, the center is a center in a width direction of the region 401A (corresponding to the "display region"). In addition, a title (Axial View, Sagittal View, or Coronal View) may be displayed on a slice image having the largest number of dipole estimation results, for example, as illustrated in FIG. 19 in order to facilitate the analyst' visual finding. In this case, when the analyst laterally scrolls from an initial display state of a slice image to display another slice image, these titles may move in conjunction with the scrolling. By moving in conjunction with the scrolling, it is possible to facilitate finding of the slice image having the largest number of dipole estimation results even after the scrolling. However, the title is preferably fixed even after the scrolling if attention is paid to the direction of a tomographic image.

Incidentally, the slice image A displayed in the display region 410A, the slice image B displayed immediately below the slice image A, and the slice image C displayed immediately below the slice image B do not correspond to the three-dimensional directions in the present embodiment. That is, for each of the display regions 410A to 410C, the slice image having the largest number of dipole estimation results 190a to be superimposed and displayed is arranged at the center among the plurality of slice images displayed in the relevant display region 410, and the other slice images are arranged so as to be aligned in the order of slice numbers laterally from the center slice image. With such display, it is possible to visually recognize the spread of the dipole estimation results 190a from the center to the left and right.

In addition, since information 440B indicating the number of dipole estimation results is also displayed in each slice image, it is possible to confirm the slice image and the dipole estimation result together when it is desired to see how many dipole estimation results are superimposed on which slice image. In addition, it is possible to know whether the dipole estimation result falls within a predetermined range (for example, within 1 mm) based on the tomographic position line 450 of the region 401B and information 440A indicating the slice number of the selected (desirably attention-paid) slice image. In addition, when it is difficult to display all the slice images in the region 401, it is also possible to display a new slice image by moving the slice image in the lateral direction, for example, by scrolling with the mouse. That is, the second display control unit 262 can perform control to display the new slice image by moving the slice image in the lateral direction in accordance with an operation (scrolling operation) to send/return the slice image.

Figure 21:
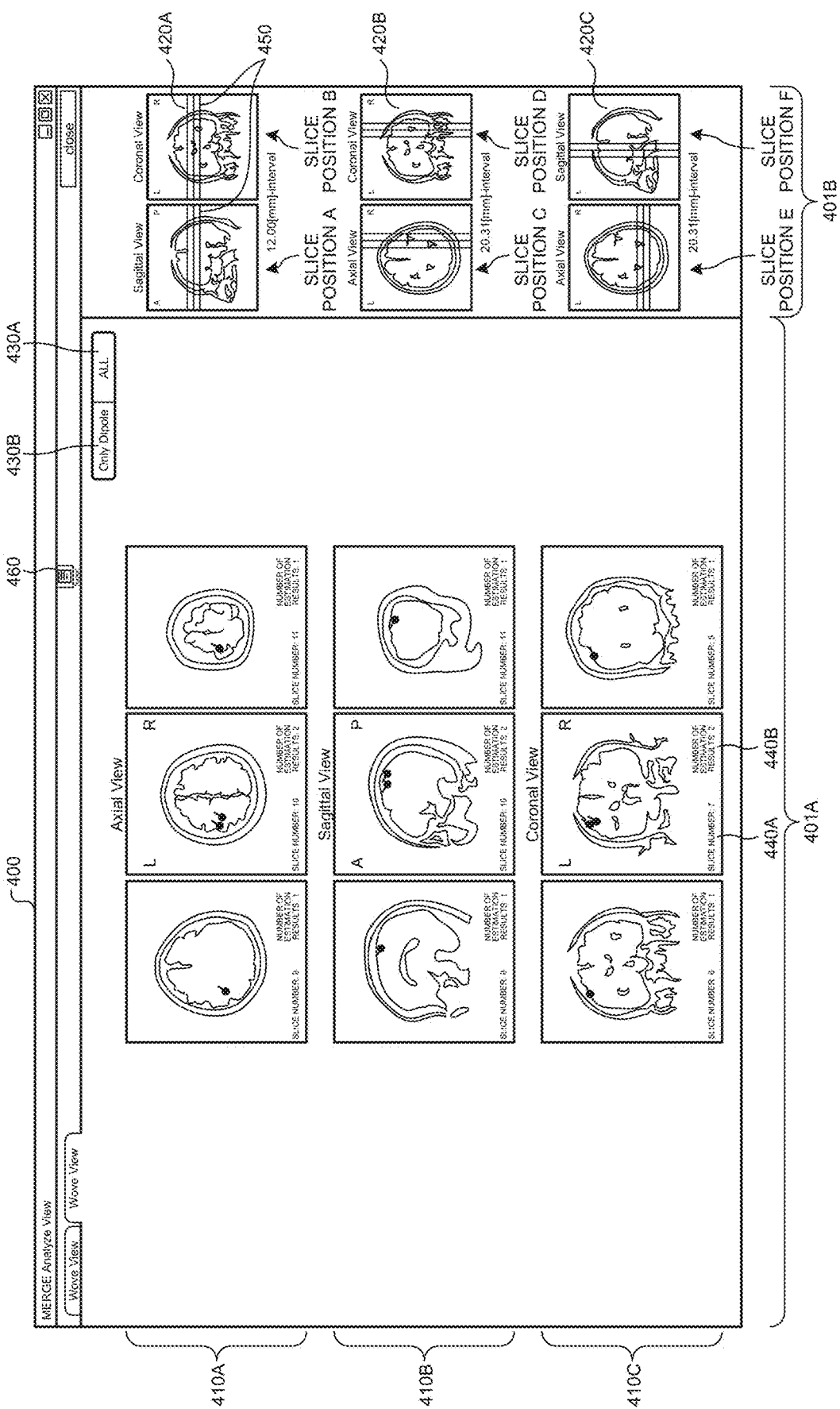
FIG. 21 is a view illustrating an example of a screen when an "only dipole" button is pressed.

In addition, an "only dipole" button 430B configured to select a mode to display only a slice image on which a dipole estimation result is superimposed and displayed, and an "all" button 430A configured to select a mode to display all the slice images including slice images on which no dipole estimation result is superimposed are arranged on the display region 410A in this example. FIG. 19 is a view illustrating an example of the screen 400 when the "all" button 430A is pressed. FIG. 21 is a view illustrating an example of the screen 400 when the "only dipole" button 430B is pressed. As illustrated in FIG. 21, only the slice image on which the dipole estimation result is superimposed and displayed is displayed in the region 401A, and the tomographic position line 450 corresponding to the slice image on which no dipole estimation result is superimposed is not displayed in the region 401B. In other words, only the tomographic position line 450 corresponding to the slice image on which the dipole estimation result is superimposed is displayed. In this manner, it is possible to easily recognize how far the respective dipole estimation results are separated by comparing the slice image to which the attention is desirably paid with the corresponding tomographic position line 450 on the same screen.

The analyst can verify at which position the dipole estimation result exists the most based on the slice image on which the dipole estimation result is superimposed and displayed. Then, when an output button 460 is pressed, the slice image on which the dipole estimation result is superimposed and displayed is output (the screen 400 at that time is output) and printed out. In this manner, a three-dimensional position of a signal source (dipole estimation result) can be specified more precisely as compared to the related art.

As described above, the condition that the slice image to be initially displayed in the region 401A needs to be the slice image having the largest number of signal sources is set, and the slice image having the largest number of signal sources is at least initially displayed in the present embodiment. Here, the second display control unit 262 initially displays the slice image having the largest number of signal sources near the center portion of the region 401A, and arranges and displays the other slice images such that the slice images are aligned in the order of layers laterally from the slice image near the center portion as described above. Since the spread of the signal sources from the center to the left and right can be visually recognized with such display, the analyst can improve the accuracy of specifying a target point that causes a case. In addition, it is possible to confirm the presence or absence of a signal source between adjacent slice images.

Incidentally, for example, a signal source (group) may be first superimposed on all slice images to generate a signal source-superimposed slice image, and a signal source-superimposed slice image having the largest number of signal sources may be selected. Such a function of selecting the signal source-superimposed slice image having the largest number of signal sources may be provided in the second display control unit 262, but the present invention is not limited thereto, and may be provided in a mode in which, for example, the above-described function is provided separately from the second display control unit 262. That is, the present invention may be provided in the mode in which the function (a selection unit) of selecting a biological tomographic image (a biological tomographic image initially displayed in the region 401A) that meets a predetermined condition is provided separately from the second display control unit 262. Incidentally, the above-described function (selection unit) may be realized by software (for example, realized as the CPU 21 executes a program), or may be realized by a dedicated hardware circuit.

In addition, for example, a signal source (group) existing in a slice image may be first specified for each of all the slice images, and a slice image having the largest number of signal sources may be selected based on a specified result, and then, a signal source may be displayed on the selected slice image in a superimposed manner. Incidentally, for example, the present invention may be provided in a mode in which the slice image (slice image having the largest number of signal sources) selected as described above is initially displayed without superimposing the signal source, and the signal source (group) or information indicating a number is superimposed and displayed at an arbitrary timing. In addition, the signal source (group) or the information indicating the number may be scroll-displayed in the display region in addition to the superimposition-display. In this case, a slice image being in a state where no signal source is superimposed and displayed can be also considered to be in a state of being potentially associated with the signal source. Thus the case of displaying such a slice image can be also considered as an example of the mode of "initially displaying the biological tomographic image on which the predetermined signal source is superimposed in the display region".

Modification 1 of First Embodiment

Figure 22:
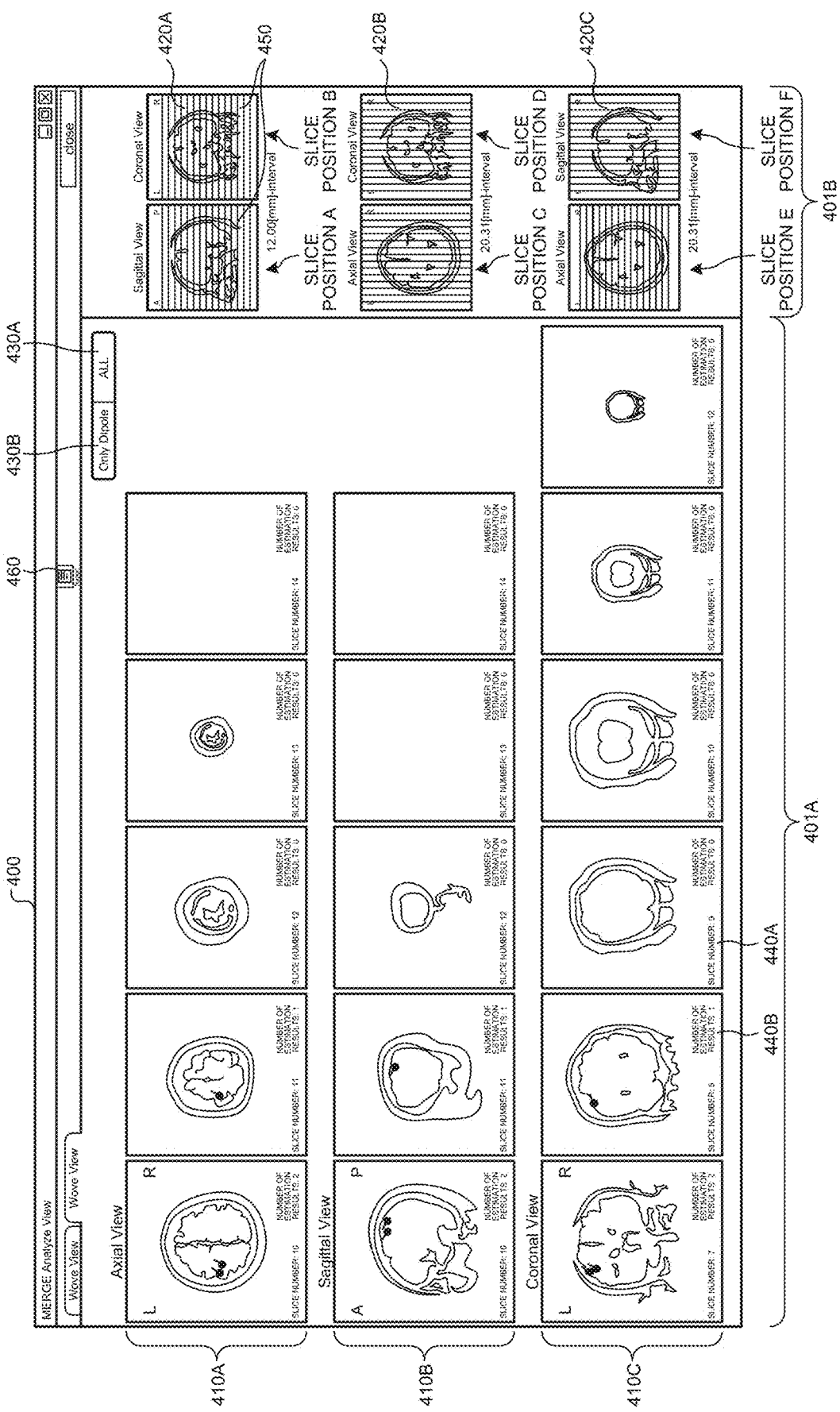
FIG. 22 is a view illustrating a screen displayed when a merge button is pressed in a modification of the first embodiment.

In the present modification, a slice image having the largest number of dipole estimation results to be superimposed and displayed is arranged on the left side among slice images displayed in the respective display regions 410A to 410C as illustrated in FIG. 22. Then, the other slice images are arranged so as to be aligned in the order of slice numbers (in the order of layers) laterally from the left slice image, which is similar to the example illustrated in FIG. 19. In the present modification, when a slice number of the slice image having the largest number of dipole estimation results is set to be the same as in FIG. 19, the screen is obtained as illustrated in FIG. 22. For example, a slice image with a slice number 10 is arranged on the left end in the display region 410A, and slice numbers 11, 12, 13, and 14 are arranged in this order on the right side thereof.

In addition, a slice image with a slice number 10 is arranged on the left end in the display region 410B, and slice numbers 11, 12, 13, and 14 are arranged in this order on the right side thereof. Further, a slice image with a slice number 7 is arranged on the left end in the display region 410C, and slice numbers 8, 9, 10, 11, and 12 are arranged in this order on the right side thereof.

In this manner, it is easy to find the slice image having the largest number of dipole estimation results by arranging the slice image having the largest number of dipole estimation results at the left end.

Modification 2 of First Embodiment

Figure 23:
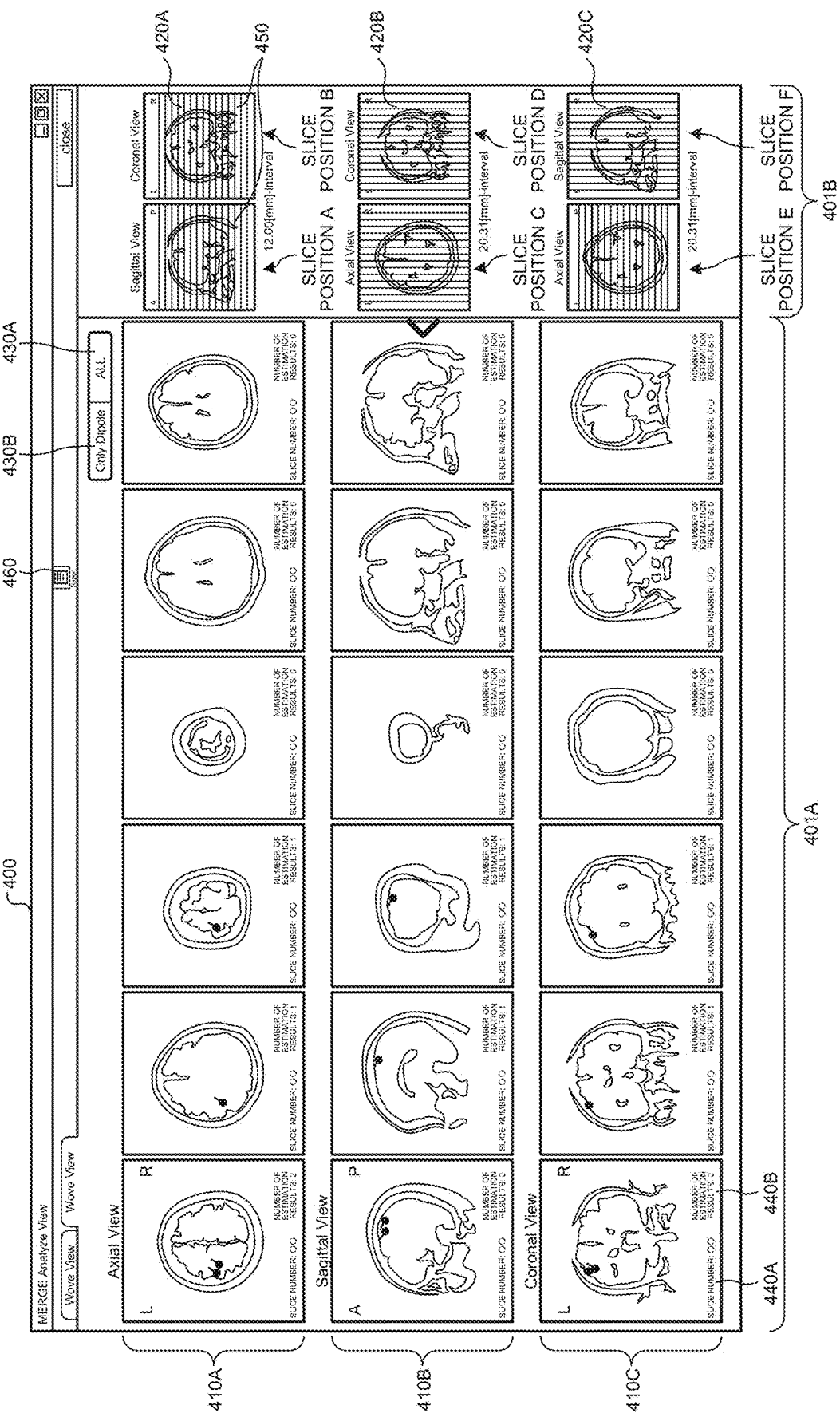
FIG. 23 is a view illustrating a screen displayed when a merge button is pressed in a modification of the first embodiment.

For example, it is also possible to display slice images (biological tomographic images) to be aligned along a predetermined direction in descending order of the number of signal sources to be superimposed on the slice image as a condition for slice images to be initially displayed in the region 401A. That is, the second display control unit 262 can also set a slice image having the largest number of signal sources (a biological tomographic image on which a predetermined signal source is superimposed) as a reference, and displays the other biological tomographic images to be aligned along the predetermined direction in descending order of the number of signal sources. For example, as illustrated in FIG. 23, the second display control unit 262 may display slice images to be aligned such that the number of signal sources to be superimposed decreases from the left to the right (an example of the predetermined direction) with arranging the slice image having the largest number of signal sources to be superimposed at a left end. It suffices to move the gaze in one direction from the left to the right of the region 401A if it is only necessary to confirm the number of signal sources (the number of dipole estimation results) on a slice image, and thus, there is also an advantage that visibility is good as compared to FIG. 19 and the like. In addition, similarly to FIG. 19, the slice image having the largest number of signal sources may be arranged at the center, and the other slice images may be arranged to be aligned such that the number of signal sources gradually decreases laterally.

Modification 3 of First Embodiment

Figure 19:
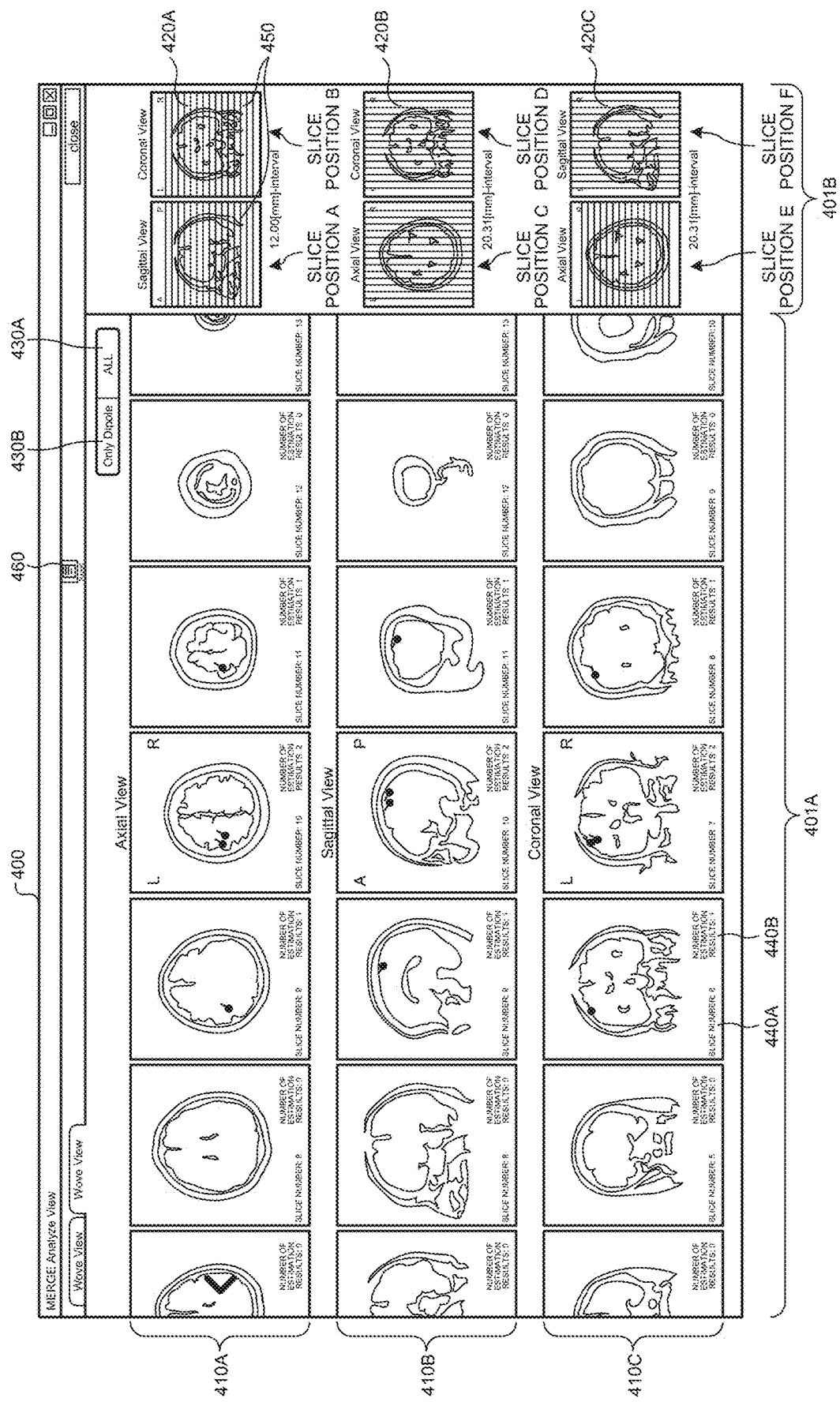
FIG. 19 is a view illustrating a screen displayed when a merge button is pressed in a first embodiment.
Figure 24:
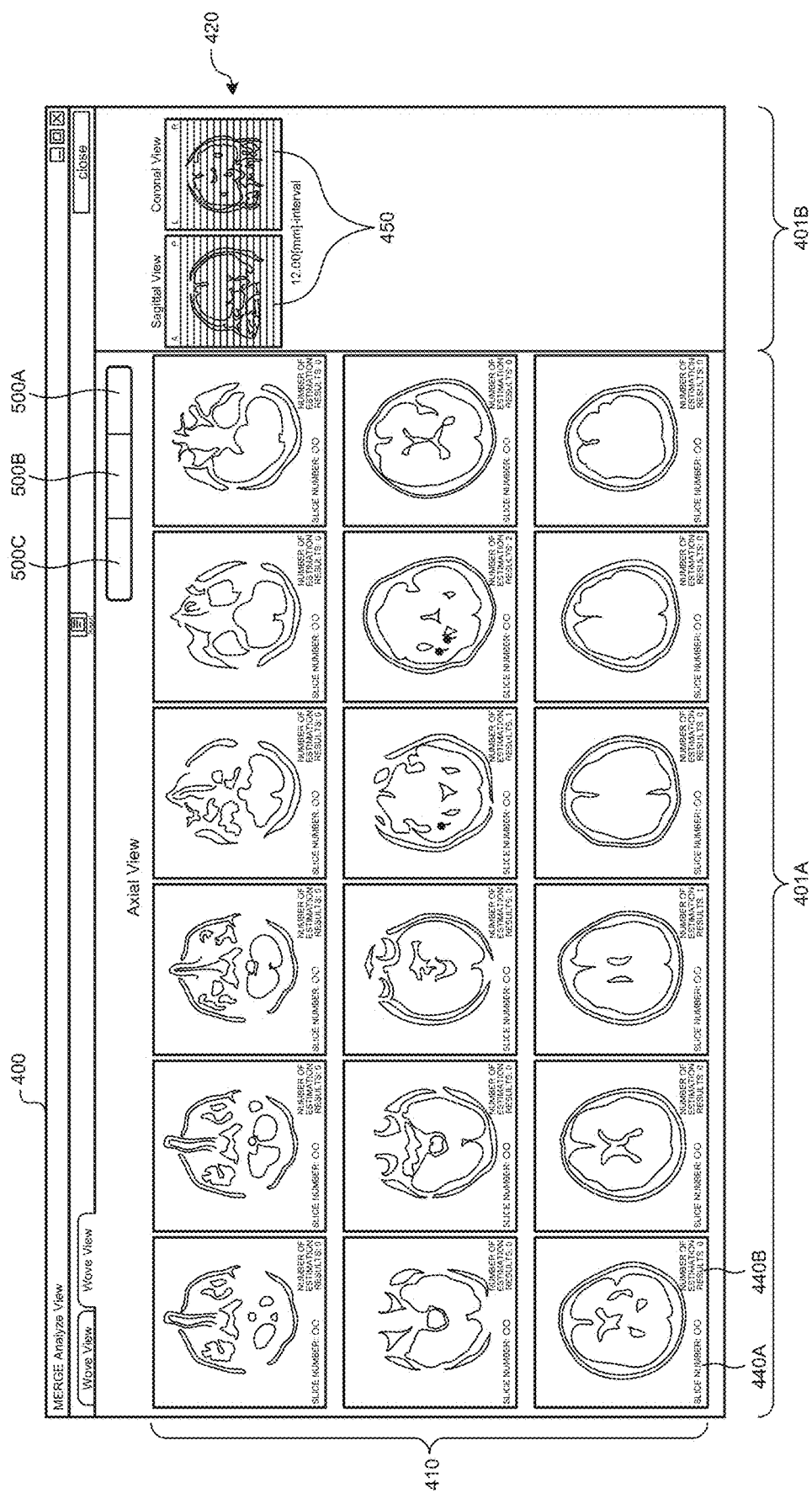
FIG. 24 is a view illustrating a screen displayed when a merge button is pressed in a modification of the first embodiment.

The slice images (the slice image A, the slice image B, and the slice image C) in three directions are displayed in the regions 410A to 410C in the example of FIG. 19 and the like. In the present modification, the second display control unit 262 displays slice images of only one direction, and does not display slice images in the other two directions. The above-described first embodiment and Modifications 1 and 2 can be applied as a condition for a slice image to be initially displayed in the region 401A at this time. For example, when the slice images are displayed in one row in the region 401A, the visibility of the slice images in one direction is improved. In addition, when there are many slice images, it is possible to reduce the number of times of scrolling by displaying tomographic images of one direction over a plurality of rows as illustrated in FIG. 24, and the entire image can be further known, and the visibility is improved. FIG. 24 is an example in which Modification 2 of the first embodiment described above is applied, that is, a slice image having the largest number of signal sources is arranged at the center and other slice images are aligned laterally such that the number of signal sources gradually decreases, and illustrates a scrolled state after initial display. Incidentally, a button 500A configured to select a direction (direction of "Axial View") corresponding to the slice image A, a button 500B configured to select a direction (direction of "Sagittal View") corresponding to the slice image B, and a button 500C configured to select a direction (direction of "Coronal View") corresponding to the slice image C are arranged on the display region 410 where the slice images of only one direction are displayed in the example of FIG. 24. The second display control unit 262 displays only a group of the slice images A when receiving the press of the button 500A, displays only a group of the slice images B when receiving the press of the button 500B, and displays only a group of the slice images C when receiving the press of the button 500C.

Modification 4 of First Embodiment

As described above, the slice image A displayed in the display region 410A, the slice image B displayed immediately below the slice image A, and the slice image C displayed immediately below the slice image B do not correspond to the three-dimensional directions in the first embodiment. However, the slice image A displayed in the display region 410A, the slice image B displayed immediately below the slice image A, and the slice image C displayed immediately below the slice image B may correspond to the three-dimensional directions as in the present modification. In this case, any one of the display regions 410A to 410C is set as a reference, a slice image having the largest number of signal sources to be superimposed is displayed at the center among a plurality of slice images displayed in the display region 410 as the reference, and the other slice images are arranged and displayed such that the slice images are aligned in the order of layers (order of slice numbers) laterally from the center slice image. Then, it is possible to arrange and display slice images of the other display regions 410 in a corresponding manner. For example, when the display region 410A is set as the reference, a slice image having the largest number of signal sources to be superimposed is displayed at the center among slice images to be displayed in the display region 410A, and the other slice images are arranged and displayed such that the slice images are aligned in the order of layers laterally from the center slice image. Then, each of a plurality of slice images to be displayed in each of the other display region 410B and display region 410C is displayed to correspond to each of the slice images displayed in the display region 410A. In this manner, it is possible to know a position of a dipole estimation result (signal source) three-dimensionally by displaying three slice images three-dimensionally corresponding to each other to be aligned in the vertical direction. In addition, a slice image having the largest number of dipole estimation results among a plurality of slice images displayed in the display region 410 serving as the reference may be arranged at the left end as in Modification 1 of the first embodiment described above.

Modification 5 of First Embodiment

In the present modification, a slice image having the largest number of signal sources to be superimposed is arranged and displayed at the center among a plurality of slice images displayed in the display region 410 serving as a reference, and the other slice images are arranged and displayed such that the number of signal sources decreases leftward and rightward from the center slice image, in Modification 4 of the first embodiment described above. Then, it is possible to display slice images of the other display regions 410 in a corresponding manner. For example, when the display region 410A is set as the reference, a slice image having the largest number of signal sources to be superimposed is displayed at the center among slice images to be displayed in the display region 410A, and the other slice images are arranged and displayed such that the slice images are aligned in a manner such that the number of signal sources decreases leftward and rightward from the center slice image. Then, each of a plurality of slice images to be displayed in each of the other display region 410B and display region 410C is displayed to correspond to each of the slice images displayed in the display region 410A. In this manner, it is possible to know a position of a dipole estimation result (signal source) three-dimensionally by displaying three slice images three-dimensionally corresponding to each other to be aligned in the vertical direction. In addition, a slice image having the largest number of dipole estimation results among a plurality of slice images displayed in the display region 410 serving as the reference may be arranged at the left end as in Modification 1.

Modification 6 of First Embodiment

In the present modification, the slice image A, the slice image B, and the slice image C corresponding to three-dimensional directions are set as one group, a group of slice images having the largest number of dipole estimation results in each group is arranged and displayed at the center, and the other groups of slice images are arranged and displayed such that the number of signal sources decreases leftward and rightward from the center slice image group. Incidentally, a slice image group having the largest number of dipole estimation results may be arranged at the left end as in Modification 1 of the first embodiment described above. In this manner, it is possible to know a position of a dipole estimation result (signal source) three-dimensionally by displaying the groups of the three slice images three-dimensionally corresponding to each other side by side.

Modification 7 of First Embodiment

The display of the slice image is switched using the "only dipole" button 430B and the "all" button 430A in the above-described first embodiment. However, the present invention may be provided in a mode in which the second display control unit 262 displays only a slice image on which a dipole estimation result is superimposed and displayed, for example, without providing these buttons.

Modification 8 of First Embodiment

The information 440A indicating the slice number is displayed in the slice image to be displayed in the region 401. However, the present invention may be provided in a mode in which the tomographic position line 450 corresponding to a slice image selected in the region 401 is highlighted and displayed (for example, displayed with a highly visible color such as "red"). Further, the above-described mode of highlight-display may be combined in addition to the information 440A indicating the slice number.

Modification 9 of First Embodiment

Figure 25:
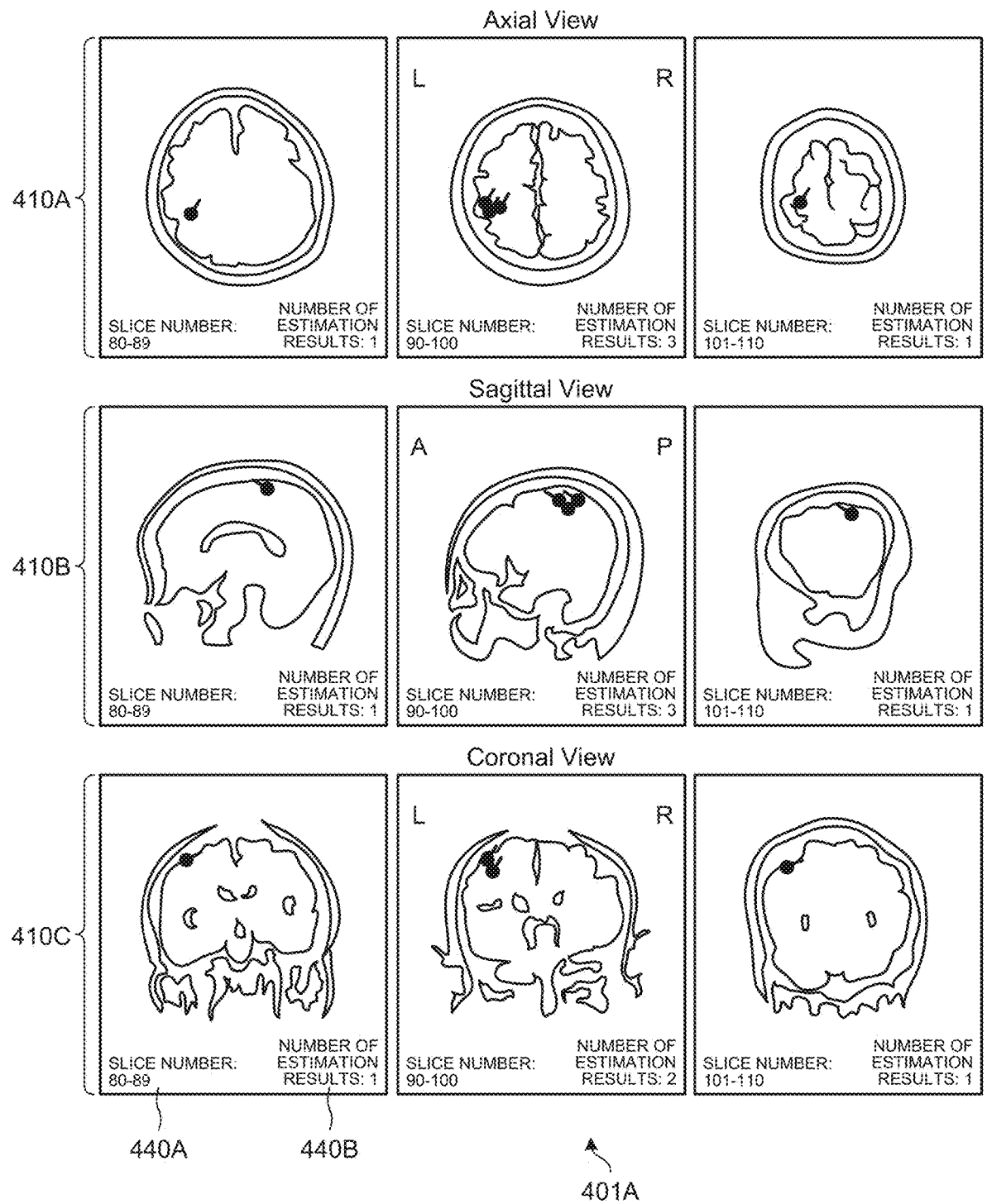
FIG. 25 is a view illustrating a screen displayed when a merge button is pressed in a modification of the first embodiment.

A signal source corresponding to one slice image is superimposed on the slice image and displayed in the region 401A in the embodiment and the respective modifications described above. In the present modification, signal sources superimposed, respectively, on a plurality of slice images are aggregated and superimposed on a predetermined slice image and displayed in the region 401. For example, each one group of ten slice images is formed in the order of slice numbers for the plurality of slice images, and a sum of the numbers of signal sources corresponding to the respective slice images included in the group is calculated for each group. Next, the sums of the numbers of signal sources of the groups are compared, and (any one of) slice images included in the group having the largest sum is displayed at the center of the region 401A as illustrated in FIG. 25. Then, slice images included in the other groups are arranged and displayed so as to be aligned in the order of slice numbers (in the order of layers) laterally from the center slice image.

Here, each slice image displayed in the region 401A is any one of the respective slice images included in the group. For example, each slice image displayed in the region 401A may be a slice image having the midst slice number among slice images having consecutive slice numbers included in a group, or may be a slice image having the smallest slice number or the largest slice number. Then, all signal sources of slice images included in a group including a slice image are superimposed on the slice image specified as the image to be displayed. In addition, when the slice number of the slice image to be displayed is determined, a slice number of slice images to be displayed on the left and right of the slice image may be a slice number shifted by the number of slice images constituting the group. For example, when one group is constituted by ten slice images, a slice number of slice images to be displayed on the left and right may be a slice number obtained by adding/subtracting ten to/from a slice number of a slice image displayed at the center.

In addition, a range of slice numbers of slice images constituting a group is displayed in the information 440A indicating the slice number as illustrated in FIG. 25. In addition, a total value of the number of signal sources corresponding to each slice image included in a group including a slice image being displayed is displayed in the information 440B indicating the number of signal sources. Incidentally, FIG. 25 illustrates an example in which only one slice image is displayed at each of the center of the region 401A and on the left and right thereof, but a plurality of slice images may be displayed in the lateral direction. According to the present modification, the total number of slice images to be displayed in the region 401A is reduced, and thus, browsability is improved as compared to the embodiment and the respective modifications described above. Incidentally, the present invention is not limited to the mode of displaying the slice image of the group having the largest total number of signal sources at the center of the region 401A, and it is also possible to apply the display mode illustrated in each of the above-described modifications to the present modification.

Modification 10 of First Embodiment

The number of signal sources to be superimposed on the slice image is used as the condition for the slice image to be initially displayed in the region 401A in the first embodiment and the respective modifications described above, but the present invention is not limited thereto. For example, it is possible to apply a condition suitable for the purpose of analysis, such as a vector direction and strength of a signal source.

As an example, it is possible to use a numerical value indicating validity or reliability of an estimated signal source, or validity or reliability of approximation of a signal source and display a slice image on which a signal source having the highest numerical value is superimposed at the center of the region 401A. The numerical value indicating validity or reliability (hereinafter collectively simply referred to as reliability) can be calculated using good of fitness (GOF) as an example. Then, a slice image on which a signal source whose calculated numerical value indicating reliability exceeds a predetermined threshold is superimposed is displayed in the region 401A. Then, a slice image on which a signal source having the largest numerical value indicating reliability (highest reliability) is superimposed is displayed in the region 401A, and other slice images are arranged and displayed so as to be aligned in the order of slice numbers (in the order of layers) on the left and right sides thereof. Incidentally, the present invention is not limited to the mode of displaying the slice image having the largest numerical value indicating reliability at the center of the region 401A, and it is also possible to apply the display mode illustrated in each of the above-described modifications to the present modification.

Figure 26:
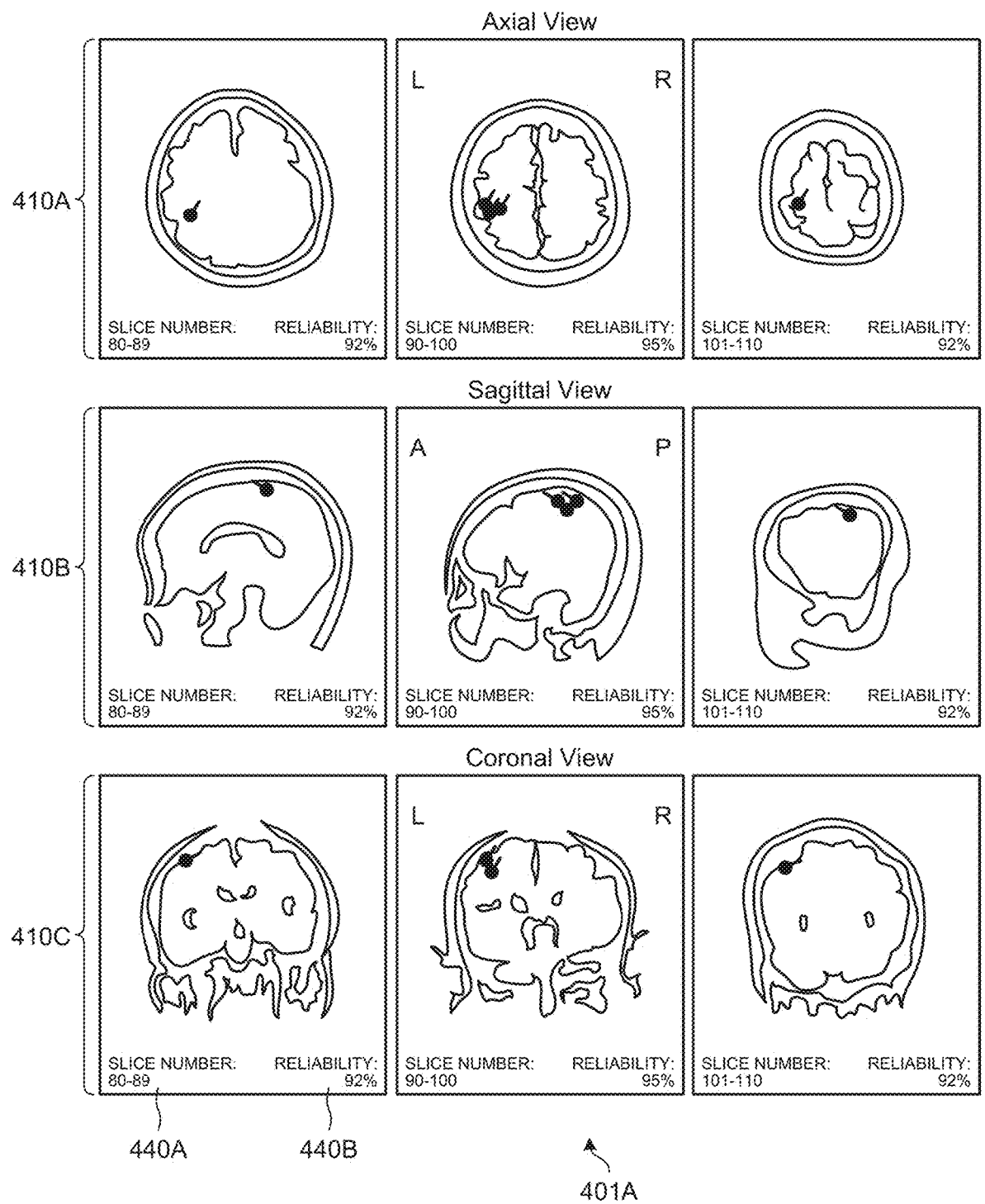
FIG. 26 is a view illustrating a screen displayed when a merge button is pressed in a modification of the first embodiment.

Here, FIG. 26 illustrates a view in which the display mode illustrated in FIG. 25 in Modification 9 described above is applied to the present modification. The present modification is different from FIG. 25 in that a number indicated in the information 440B is not the number of signal sources but the numerical value indicating reliability. In addition, the numerical value indicating reliability illustrated in FIG. 26 may be an average value of reliability of each signal source to be superimposed on slice images included in one group, or may be a numerical value of a signal source having the highest numerical value indicating reliability among the signal sources to be superimposed on slice images included in one group.

According to the present modification, the accuracy of specifying a target point that causes a case is further improved by specifying a highly reliable signal source. In addition, the number indicated in the information 440B may be set to the number of signal sources as illustrated in FIG. 25, and a representation (a color, a shape, a size, or the like) of a signal source may be distinguished using a representation in accordance with a GOF value.

Modification 11 of First Embodiment

The operation of displaying the signal source whose numerical value indicating reliability is equal to or higher than the predetermined threshold on the slice image in a superimposed manner has been illustrated in Modification 10, but the present invention is not limited thereto. For example, an image having low reliability is also displayed in this modification. In this case, a slice image on which a signal source whose numerical value indicating reliability is equal to or higher than the predetermined threshold is superimposed is displayed to be distinguished from a slice image having the low reliability. For example, a background color of the slice image may be changed between a numerical value equal to or higher than the threshold and a numerical value lower than the threshold, a color of an outer peripheral frame of a slice image may be changed, or a mark for calling attention may be displayed inside a slice image. In addition, when a signal source having a numerical value equal to or higher than the threshold and a signal source having a numerical value lower than the threshold are superimposed on a slice image, representations (colors, shapes, sizes, or the like) of the signal sources may be displayed to be distinguished between the numerical value equal to or higher than the threshold and the numerical value lower than the threshold.

Modification 12 of First Embodiment

As another example different from Modification 10, an average coordinate of all signal sources is calculated, and a slice image corresponding to the average coordinate is arranged at the center of the region 401A in this modification. Then, the other slice images are arranged and displayed so as to be aligned in the order of slice numbers (in the order of layers) on the left and right of the slice image displayed at the center. As a result, it is easy to visually recognize the spread of positions of the respective signal sources from the average coordinate. Incidentally, the present invention is not limited to the mode of displaying the slice image corresponding to the average coordinate at the center of the region 401A, and it is also possible to apply the display mode illustrated in each of the above-described modifications to the present modification.

As still another example, a median number between the maximum number and the minimum number among slice numbers of the respective slice images in which signal sources are present may be calculated, a slice image corresponding to the median number may be displayed at the center of the region 401A, and the other slice images may be arranged and displayed so as to be aligned in the order of slice numbers (in the order of layers) on the left and right sides thereof. As a result, it is easy to visually recognize the spread from the center of a target point. Also in this example, the present invention is not limited to the mode of displaying the slice image corresponding to a central coordinate at the center of the region 401A, and it is also possible to apply the display mode illustrated in each of the above-described modifications to the present modification.

Second Embodiment

Next, a second embodiment will be described. Parts common to the above-described respective embodiments will not be described as appropriate. A basic device configuration is the same as that in the above-described first embodiment. The biological data for a predetermined time length (which can be regarded as "a piece of biological data") is displayed on the analysis screen in the above-described respective embodiments. In the present embodiment, however, the first display control unit 261 sets a plurality of pieces of biological data delimited for each predetermined time length as display targets, and displays a signal waveform of any biological data corresponding to a time zone 120b.

In addition, the analysis unit 252 (estimation unit) estimates a signal source corresponding to an annotation selected from among a plurality of annotations that have been already input with respect to biological data, for each of the plurality of pieces of biological data delimited for each predetermined time length. Then, the second display control unit 262 variably controls display of one or more biological tomographic images based on the number of signal sources corresponding to some of the plurality of pieces of biological data. In this example, the second display control unit 262 performs control so as to display the signal sources corresponding to some of the plurality of pieces of biological data delimited for each predetermined time length on a plurality of sliced biological tomographic image in a superimposed manner, and to initially display a biological tomographic image in which a predetermined signal source is superimposed in a display region among the plurality of sliced biological tomographic images similarly to the above-described first embodiment. Hereinafter, the specific contents will be described.

<Operation During Measurement Recording>

Figure 27:
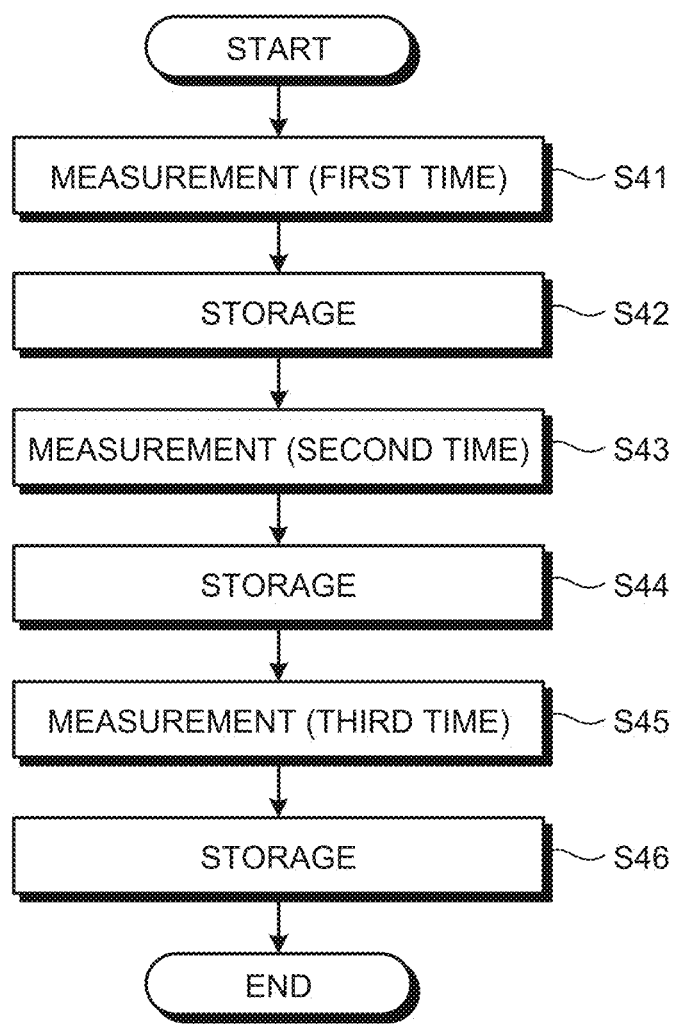
FIG. 27 is a flowchart illustrating an operation example (an operation at the time of measurement recording for three times) of an information processing apparatus of a second embodiment.

For example, it is assumed that the measurement operation that has been described in the first embodiment is intermittently performed three times. It is assumed that a predetermined interval (an interval time is arbitrary) is provided between the respective measurements. Incidentally, the number of times such as "three times" is an example, and the present invention is not limited thereto. In short, the number of times of measurements can be changed arbitrarily according to the purpose of an examination. FIG. 27 is a flowchart illustrating an operation example (an operation during measurement recording performed three times) of the information processing apparatus 50 in this case. As illustrated in FIG. 27, the information processing apparatus 50 performs the first measurement in Step S41. An operation at this time is the same as the processing from Step S12 to Step S17 in FIG. 8. Then, when the first measurement is completed, the information processing apparatus 50 stores measurement data including biological data obtained by the first measurement and an input annotation in the recording/analysis information storage unit 254 in association with a subject ID to identify a subject (Step S42).

Next, the information processing apparatus 50 performs the second measurement (Step S43). An operation at this time is the same as the processing from Step S12 to Step S17 in FIG. 8. Then, when the second measurement is completed, the information processing apparatus 50 stores measurement data including biological data obtained by the second measurement and an input annotation in the recording/analysis information storage unit 254 in association with the subject ID (Step S44).

Next, the information processing apparatus 50 performs the third measurement (Step S45). An operation at this time is the same as the processing from Step S12 to Step S17 in FIG. 8. Then, when the third measurement is completed, the information processing apparatus 50 stores measurement data including biological data obtained by the third measurement and an input annotation in the recording/analysis information storage unit 254 in association with the subject ID (Step S46).

In the above-described manner, each time one-time measurement (measurement over a predetermined time length) is completed, measurement data indicating a result of the measurement is stored in the recording/analysis information storage unit 254 in the unit of files. In the following description, a file of one piece of measurement data stored in the recording/analysis information storage unit 254 will be sometimes referred to as a "measurement file". In this example, three measurement files are stored in the recording/ analysis information storage unit 254 after the three times of measurements are completed. Hereinafter, a measurement file corresponding to the first measurement, a measurement file corresponding to the second measurement, and a measurement file corresponding to the third measurement will be sometimes referred to as a first measurement file, a second measurement file, and a third measurement file, respectively. As described above, each measurement file is stored in the recording/analysis information storage unit 254 in association with the subject ID.

<Operation During Analysis>

Figure 28:
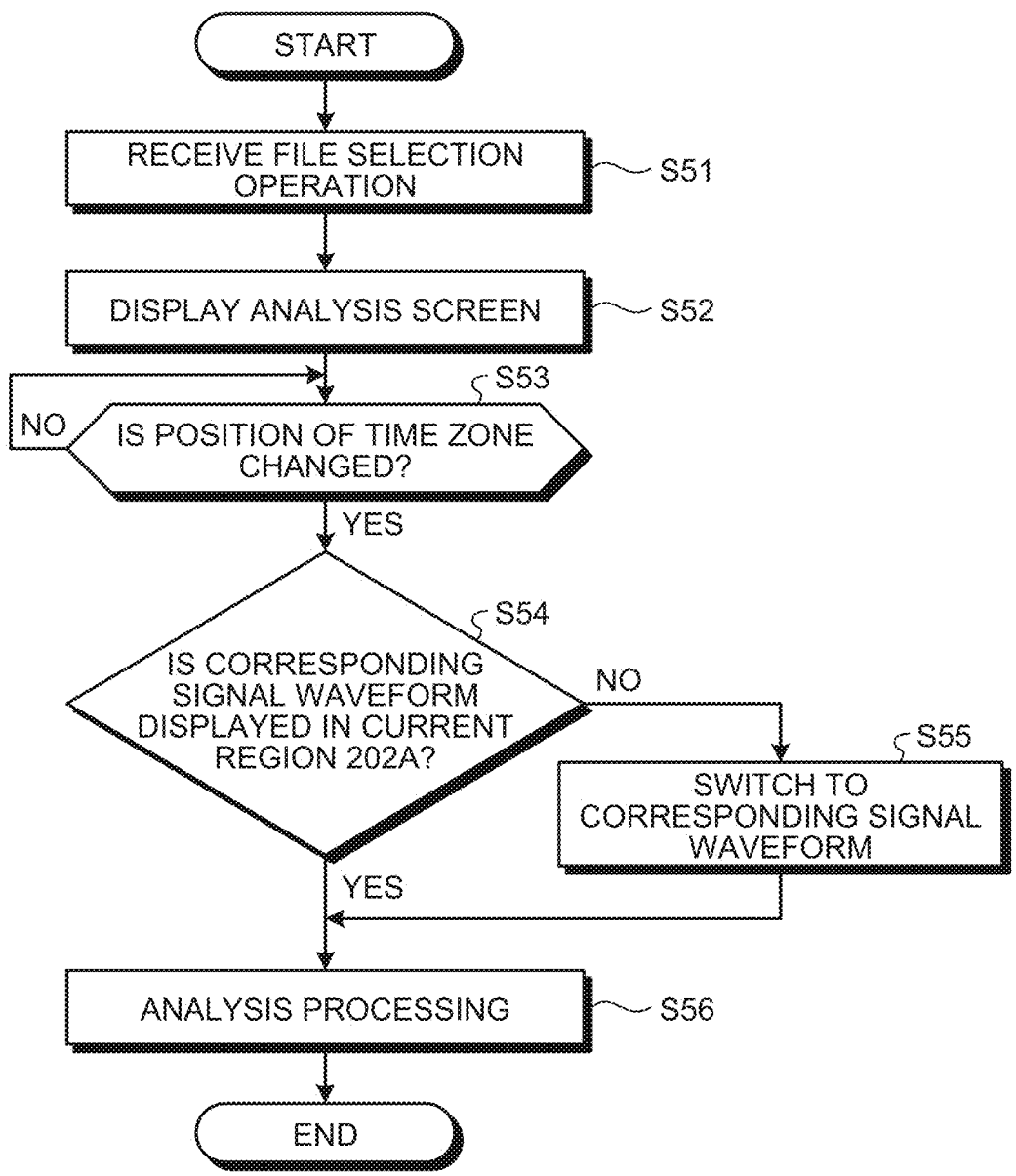
FIG. 28 is a flowchart illustrating an operation example of the information processing apparatus according to the second embodiment.

Next, an operation during analysis will be described. Here, it is assumed that the information processing apparatus 50 (the first display control unit 261) displays a selection screen, configured to select a measurement file obtained by a measurement, on the display device 28 when receiving the press of the "analysis" button on the start screen 204 of FIG. 2. FIG. 28 is a flowchart illustrating an operation example of the information processing apparatus 50 at this time.

First, the information processing apparatus 50 (the first display control unit 261) receives an operation of selecting a measurement file from the selection screen (Step S51). Next, the information processing apparatus 50 (the first display control unit 261) reads a series of measurement files (the above-described three measurement files in this example) including the measurement file selected in Step S51 and one or more other measurement files with which a subject ID, which is the same as a subject ID associated with the measurement file, is associated, and performs control to display an analysis screen on which the series of read measurement files has been reflected on the display device 28 (Step S52).

Figure 29:
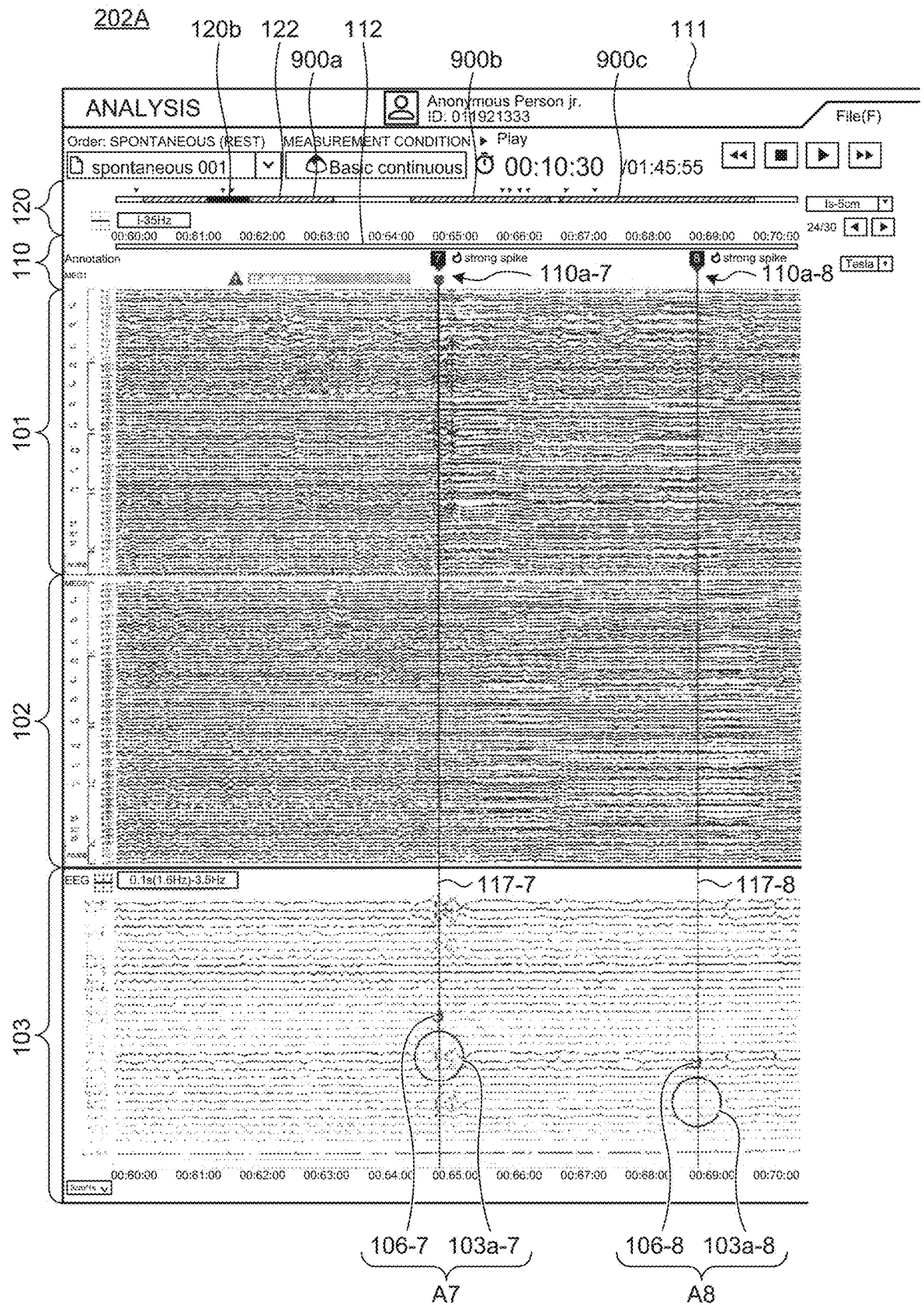
FIG. 29 is a view illustrating a region on the left side of an analysis screen in the second embodiment.

FIG. 29 is a view illustrating an example of the region 202A on the left side of the analysis screen at this time. A total time including a total recording time of a series of measurement files (the first measurement file, the second measurement file, and the third measurement file) is displayed on the time axis 122 instead of a total recording time corresponding to any one measurement file. Further, range information 900a indicating a recording period of the first measurement file, range information 900b indicating a recording period of the second measurement file, and range information 900c indicating a recording period of the third measurement file are displayed on the time axis 122. In the following description, the range information 900a, 900b, and 900c will be sometimes simply referred to as "range information 900" when not distinguished from each other. The present invention may be provided in a mode in which each of the range information 900 is added with information indicating a name of a corresponding measurement file. In this example, since the respective measurements are performed at intervals, a gap (blank region) is provided between pieces of the range information 900 on the time axis 122. The analyst can switch a signal waveform to be displayed in the region 202A by performing an operation of moving the time zone 120b using a mouse or the like. In this example, a signal waveform (a part of biological data of any measurement file) corresponding to the time zone 120b is displayed in the region 202A. That is, the analyst can display a signal waveform in a desired time zone in the region 202A straddling the measurement files by moving the time zone 120b on the time axis 122. In addition, here, all annotations included in each of the three measurement files are displayed in the annotation list 180 of the region 202B on the right side of this analysis screen. In addition, the present invention may be provided in a mode in which, for example, a name of a target examination is associated with each measurement file, and a name of an examination corresponding to the time zone 120b is also displayed on the analysis screen.

The description will be continued returning to FIG. 28. When receiving an operation to change a position of the time zone 120b (Step S53: Yes) after the analysis screen is displayed in Step S52, the information processing apparatus 50 (the first display control unit 261) confirms whether a signal waveform corresponding to the changed position of the time zone 120b is displayed in the current region 202A (Step S54).

When the result of Step S54 is negative (Step S54: No), the information processing apparatus 50 (the first display control unit 261) switches the signal waveform displayed in the region 202A to the signal waveform corresponding to the changed position of the time zone 120b (Step S55). When the result of Step S54 is positive (Step S54: Yes), or after Step S55, the information processing apparatus 50 executes analysis processing in accordance with an operation of the analyst (Step S56). The content of this analysis processing is the processing from Step S23 to Step S31 illustrated in FIG. 15. Incidentally, all the annotations included in each of the three measurement files are displayed in the annotation list 180 as described above. Then, when receiving the press of the merge button 300 in Step S29, the second display control unit 262 performs control to display a plurality of biological tomographic images on which each of a plurality of signal sources having one-to-one correspondence with a plurality of annotations added with the estimation completion mark 182 is superimposed, among the plurality of annotations (all the annotations straddling the plurality of measurement files) displayed in the annotation list 180, to be aligned in accordance with the number of signal sources to be superimposed on each of the plurality of biological tomographic images. In short, a set of signal sources to be superimposed on each slice image illustrated in FIG. 19 is the plurality of signal sources having one-to-one correspondence with the plurality of annotations for which the signal source has been estimated among all the annotations straddling the plurality of measurement files.

Modification 1 of Second Embodiment

Figure 30:
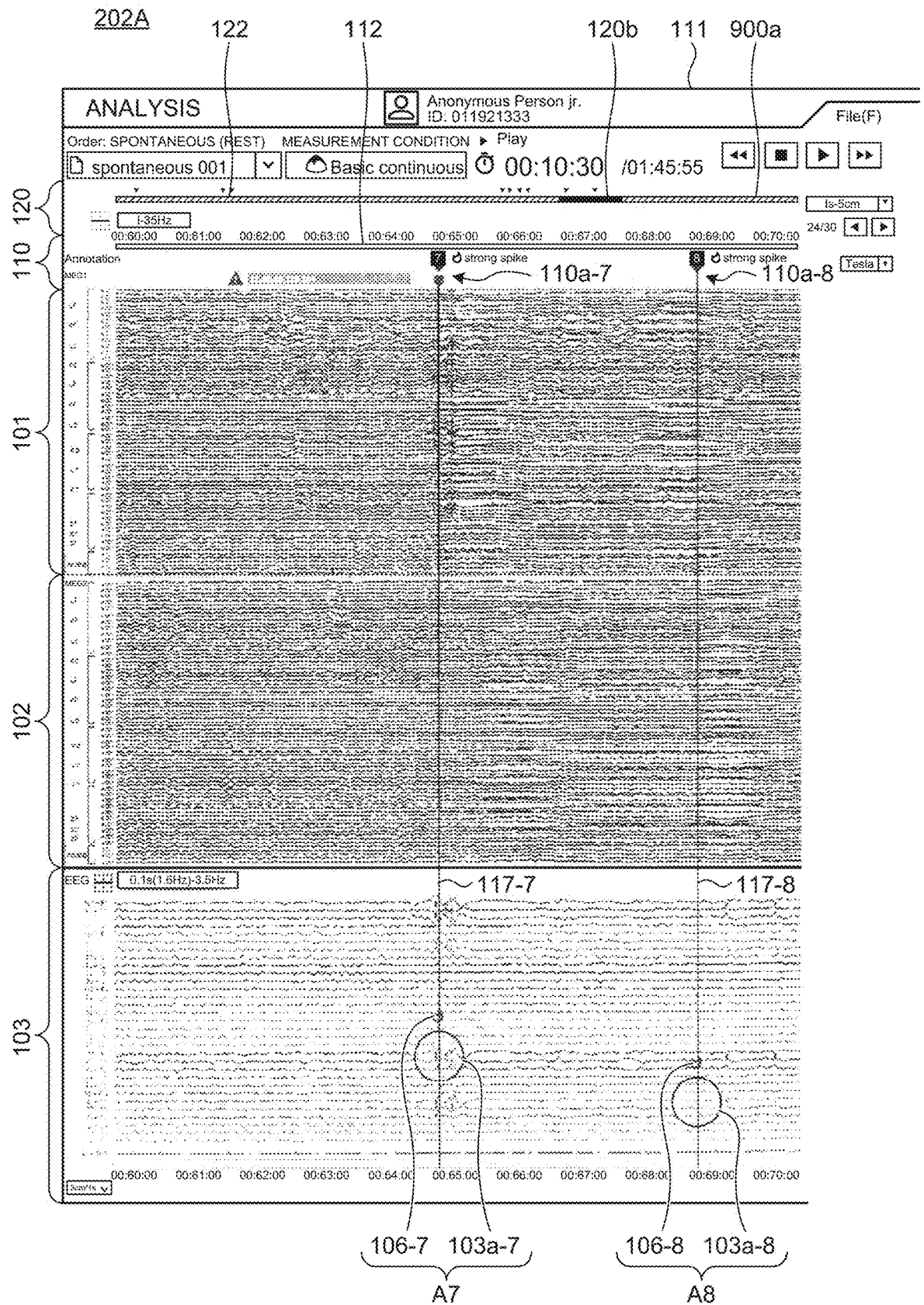
FIG. 30 is a view illustrating an example of an analysis screen of a modification of the second embodiment.

For example, the present invention may be provided in a mode in which only the range information 900 corresponding to any one measurement file is displayed on the time axis 122 of the analysis screen, and the range information 900 on the time axis 122 is switched in the unit of measurement files in accordance with an operation of the analyst. FIG. 30 is a view illustrating an example of the analysis screen. In the example of FIG. 30, only the range information 900a indicating the recording period of the first measurement file is displayed on the time axis 122. When receiving an operation to switch the range information 900 performed by the analyst, the information processing apparatus 50 (the first display control unit 261) switches the range information 900 on the time axis 122 in the unit of measurement files in accordance with the received operation, and switches display of the display region 202A and the display region 202B in accordance with the switched measurement file.

Modification 2 of Second Embodiment

The position of the time zone 120b is set so as not to straddle different pieces of the range information 900 in the above-described second embodiment. For example, when receiving an operation of sending the position of the time zone 120b by one stage in a state where the time zone 120b is positioned at an end point of the range information 900a illustrated in FIG. 29, the information processing apparatus 50 (the first display control unit 261) switches display of the time zone 120b such that the time zone 120b is positioned at a start point of the subsequent range information 900b without straddling the range information 900a and the range information 900b.

Figure 31A:
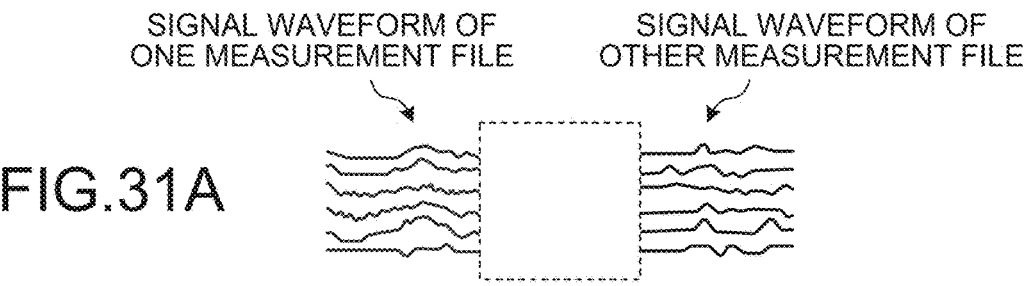
FIGS. 31A to 31E are views for describing display methods of distinguishing signal waveforms for each different range information.
Figure 31B:
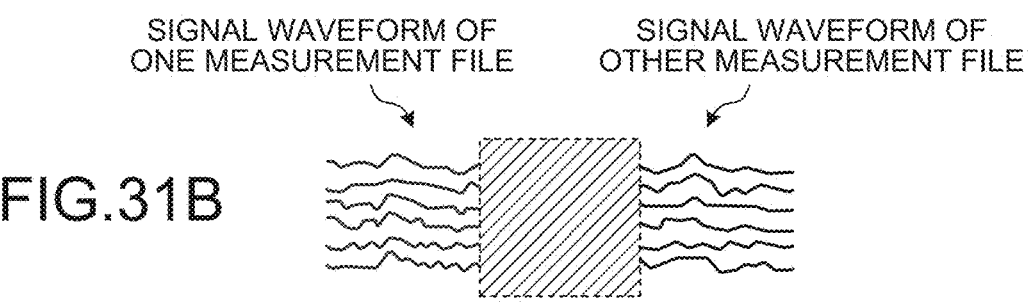

However, the present invention is not limited thereto, and the time zone 120b is also allowed to be arranged so as to straddle different pieces of the range information 900 in this modification. In this case, a signal waveform corresponding to the time zone 120b has a blank region (corresponding to a gap between measurements) in which no biological signal exists as illustrated in FIG. 31A. For example, the information processing apparatus 50 (the first display control unit 261) may perform display by changing the background of the blank region in order to facilitate visual recognition of a region between different measurement files as illustrated in FIG. 31B.

Figure 31C:
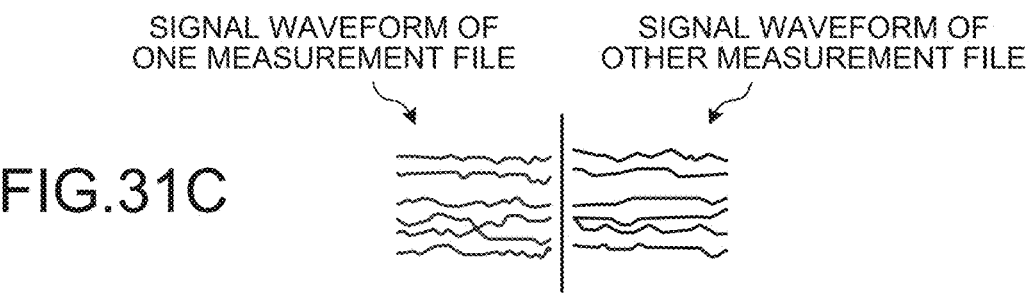
Figure 31D:
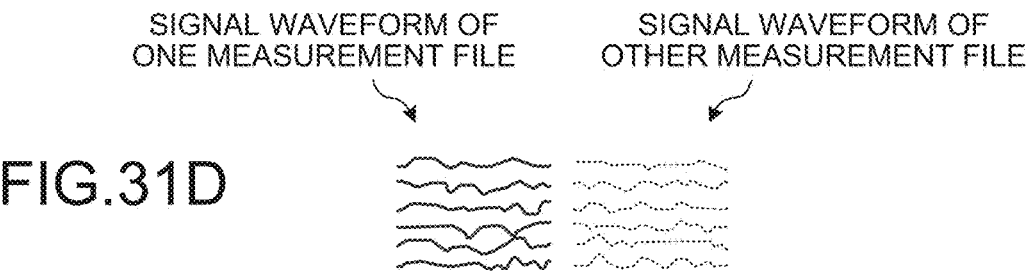
Figure 31E:
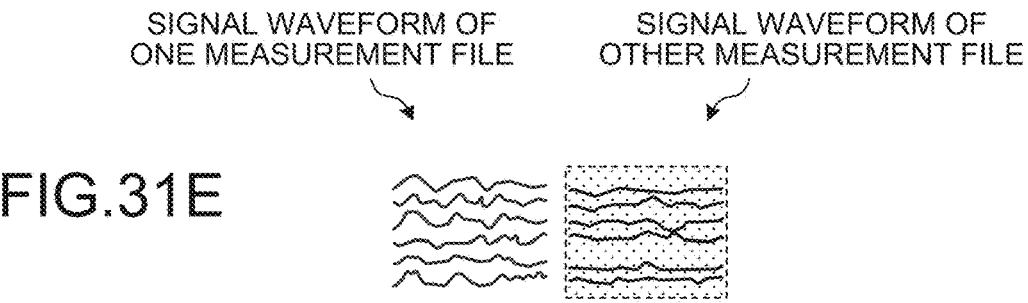

In addition, it is assumed that there is almost no gap between a signal waveform corresponding to one measurement file and a signal waveform corresponding to the other measurement file, for example, when the time zone 120b is arranged so as to straddle different pieces of the range information 900 and the time interval between measurements is short. In such a case, the information processing apparatus 50 (the first display control unit 261) may display a line (line different from the annotation line) representing a joint between the signal waveform corresponding to one measurement file and the signal waveform corresponding to the other measurement file, for example, as illustrated in FIG. 31C Further, the information processing apparatus 50 may perform different display for the signal waveform corresponding to one measurement file and the signal waveform corresponding to the other measurement file, for example, as illustrated in FIG. 31D, and may change a color of the background of a signal waveform corresponding to any measurement file, for example, as illustrated in FIG. 31E.

Modification 3 of Second Embodiment

Figure 32:
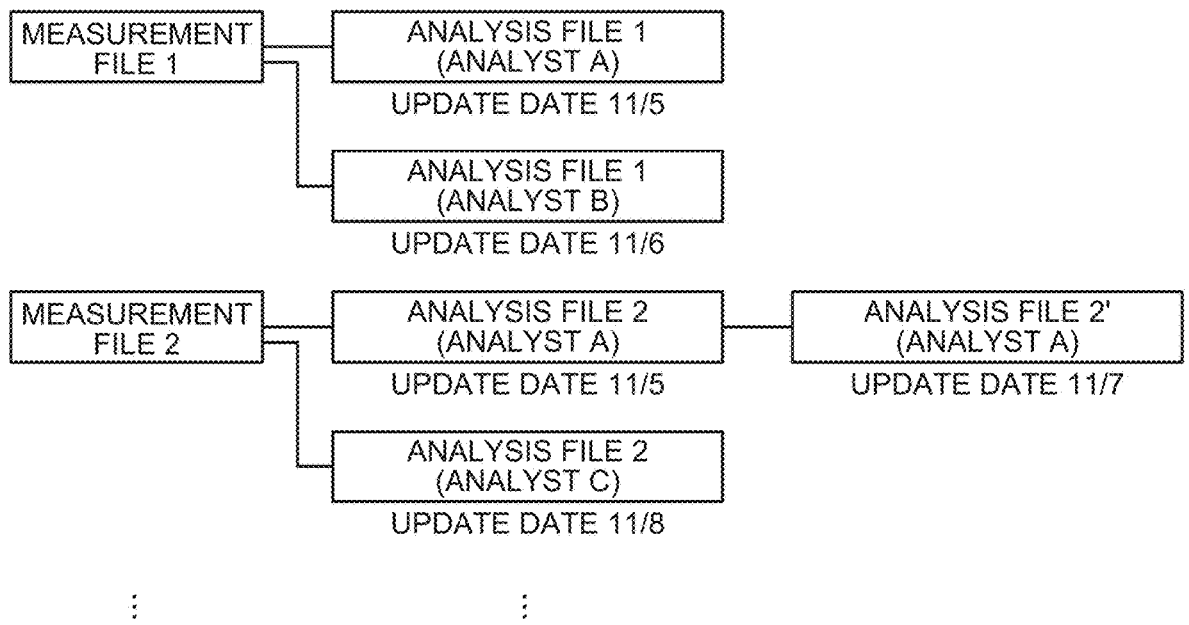
FIG. 32 is a schematic view illustrating a state where analysis files are managed in association with each of a plurality of measurement files.

As illustrated in FIG. 32, the information processing apparatus 50 of the second embodiment manages (stores) an analysis file indicating an analysis result (analysis information) for each of a plurality of measurement files in an associated manner. Here, the number of analysts is not limited to one, and it is also assumed that each of a plurality of analysts performs analysis. In this case, a different analysis file is generated for each of the plurality of analysts and is associated with the measurement file. In addition, each time analysis is completed, an analysis file indicating an analysis result at that time is newly associated with the measurement file in this example. That is, when receiving the input of the analysis end command every one-time analysis, the information processing apparatus 50 newly stores the analysis file indicating the analysis result at that time in association with the measurement file. For example, the present invention may be provided in a mode in which the analysis end command is input by being triggered as the pressing of a button indicating "store" or "end" on the analysis screen performed by an analyst.

Here, when annotations of all files are displayed in the annotation list 180 of the analysis screen, an analyst who is currently logging in and performing analysis is provided with annotations that have not been analyzed by himself, and it is necessary to find out an annotation that has been analyzed by himself from among all the annotations, thereby causing a great burden.

Figure 33:
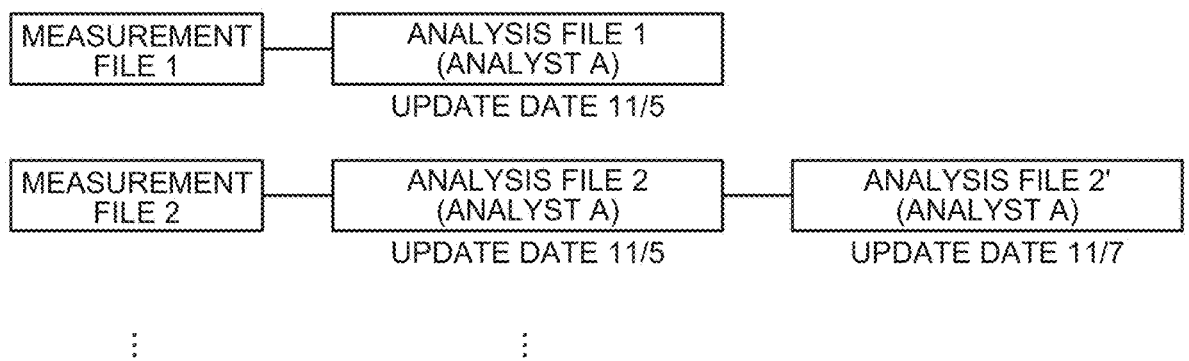
FIG. 33 is a view illustrating an example of a selection screen in a modification of the second embodiment.

Thus, the information processing apparatus 50 manages an analyst, an update date (a creation date of an analysis file), and a subject ID in an associated manner for each analysis file in the present modification. Then, the information processing apparatus 50 (the first display control unit 261) extracts an analysis file corresponding to an analyst who is logging in from among analysis files included in a file list as illustrated in FIG. 32 when receiving the press of the "analysis" button on the start screen 204 of FIG. 2, and displays a selection screen in which the extracted analysis file is associated with each of the plurality of measurement files on the display device 28. Incidentally, as for the measurement file with which the extracted analysis file is not associated, only the measurement file is displayed. For example, when the analyst who is logging in is an analyst "A", an analysis file corresponding to the analyst "A" is extracted from the analysis files included in the file list of FIG. 32, and the selection screen as illustrated in FIG. 33 is displayed.

When receiving the selection of any measurement file from this selection screen, the information processing apparatus 50 displays an analysis screen on which a series of measurement files including the selected measurement file and one or more other measurement files associated with a subject ID, which is the same as a subject ID associated with the selected measurement file, has been reflected. Here, when displaying the annotation list 180 on this analysis screen, the information processing apparatus 50 (the first display control unit 261) specifies an analysis file associated with the measurement file for each of the series of measurement files, and displays an annotation corresponding to the specified analysis file in the annotation list 180. In addition, when a plurality of analysis files of the same analyst are associated with one measurement file, only an analysis file of the latest update date is specified, and an annotation corresponding to the specified analysis file is displayed in the annotation list 180. In addition, when no analysis file is associated with one measurement file, an annotation included in the measurement file is displayed in the annotation list 180.

In addition, the present invention may be provided in a mode in which, for example, the analyst selects all measurement files desirably set as display targets on the selection screen. For example, the information processing apparatus 50 (the first display control unit 261) may display an analysis screen on which only a measurement file 2 has been reflected when the analyst "A" selects the measurement file 2 on the selection screen of FIG. 33. Here, when displaying the annotation list 180 on this analysis screen, the information processing apparatus 50 (the first display control unit 261) displays an annotation corresponding to an analysis file 2' of the latest update date in the annotation list 180 between two analysis files 2 and 2' associated with the measurement file 2.

Since only the annotation corresponding to the analyst who is logging in is properly displayed in the annotation list 180 of the analysis screen as above, the convenience of the analyst is improved.

Incidentally, logging-in means being authorized to use the information processing apparatus 50, and the information processing apparatus 50 has a function of determining whether to permit login of a user (analyst). For example, when the information processing apparatus 50 is activated, a login screen to promote input of information for logging-in (for example, login information including a combination of an ID and a password) is displayed, and the analyst inputs his own login information on the login screen. The information processing apparatus 50 registers the login information set in advance for each user having usage authority in an associated manner, and permits logging-in of the user (analyst) who has input login information when the login information input through the login screen matches the registered login information, and does not permit the logging-in when both the pieces of the login information do not match.

Although the embodiments according to the present invention have been described as above, the present invention is not limited directly to the above-described embodiment, and constituent elements thereof can be modified and embodied at an implementation stage within a scope not departing from a gist thereof. In addition, various inventions can be formed by appropriately combining a plurality of constituent elements disclosed in the above-described embodiments. For example, some constituent elements may be deleted from all the constituent elements illustrated in the above-described embodiments. Further, constituent elements according to different embodiments and modifications may be appropriately combined.

In addition, the program to be executed by the biological signal measurement system 1 of the above-described respective embodiments may be configured to be provided in the state of being recorded in a computer-computer readable recording medium such as a CD-ROM, a flexible disk (FD), a CD-R, a digital versatile disk (DVD), and a universal serial bus (USB) in an installable or executable file format, or may be configured to be provided or distributed via a network such as the Internet. In addition, various programs may be configured to be provided in the state of being incorporated in a ROM or the like in advance.

According to an embodiment, it is possible to improve the accuracy of specifying the target point that causes the case.

The above-described embodiments are illustrative and do not limit the present invention. Thus, numerous additional modifications and variations are possible in light of the above teachings. For example, at least one element of different illustrative and exemplary embodiments herein may be combined with each other or substituted for each other within the scope of this disclosure and appended claims. Further, features of components of the embodiments, such as the number, the position, and the shape are not limited the embodiments and thus may be preferably set. It is therefore to be understood that within the scope of the appended claims, the disclosure of the present invention may be practiced otherwise than as specifically described herein.

The method steps, processes, or operations described herein are not to be construed as necessarily requiring their performance in the particular order discussed or illustrated, unless specifically identified as an order of performance or clearly identified through the context. It is also to be understood that additional or alternative steps may be employed.

Further, any of the above-described apparatus, devices or units can be implemented as a hardware apparatus, such as a special-purpose circuit or device, or as a hardware/software combination, such as a processor executing a software program.

Further, as described above, any one of the above-described and other methods of the present invention may be embodied in the form of a computer program stored in any kind of storage medium. Examples of storage mediums include, but are not limited to, flexible disk, hard disk, optical discs, magneto-optical discs, magnetic tapes, non-volatile memory, semiconductor memory, read-only-memory (ROM), etc.

Alternatively, any one of the above-described and other methods of the present invention may be implemented by an application specific integrated circuit (ASIC), a digital signal processor (DSP) or a field programmable gate array (FPGA), prepared by interconnecting an appropriate network of conventional component circuits or by a combination thereof with one or more conventional general purpose microprocessors or signal processors programmed accordingly.

Each of the functions of the described embodiments may be implemented by one or more processing circuits or circuitry. Processing circuitry includes a programmed processor, as a processor includes circuitry. A processing circuit also includes devices such as an application specific integrated circuit (ASIC), digital signal processor (DSP), field programmable gate array (FPGA) and conventional circuit components arranged to perform the recited functions.

REFERENCE SIGNS LIST

1 Biological signal measurement system
3 Measurement device
21 CPU
22 RAM
23 ROM
24 Auxiliary storage device
25 Input/output interface
27 Bus
28 Display device
40 Server
50 Information processing apparatus
250 Control unit
251 Display control unit
252 Analysis unit
253 Sensor information acquisition unit
254 Recording/analysis information storage unit
255 Annotation input unit
261 First display control unit
262 Second display control unit

What is claimed is:
1. An information processing apparatus, comprising:
a display control unit configured to perform control to display, in a region of an analysis screen displayed by a display device, one or more signal sources in a superimposed manner on a plurality of sliced biological tomographic images, of a brain of a human subject, that are sliced in a particular direction, each signal source corresponding to a part of biological data indicating a temporal change of a biological signal and representing a dipole estimation result determined based on the biological data, each signal source superimposed at a particular position on at least one sliced biological tomographic image to indicate a point position associated with the signal source in an image portion of the brain of the human subject that is shown in the at least one sliced biological tomographic image, and display, in a display region of a display screen displayed by the display device, two or more sliced biological tomographic images of the plurality of sliced biological tomographic images, such that the two or more sliced biological tomographic images are arranged in a certain direction in the display region of the display screen, wherein the two or more sliced biological tomographic images include a particular sliced biological tomographic image, of the plurality of sliced biological tomographic images, that is displayed in the display region in accordance with a particular condition, and other sliced biological tomographic images of the two or more sliced biological tomographic images are arranged in the certain direction in relation to the particular sliced biological tomographic image in the display region of the display screen.

2. The information processing apparatus according to claim 1, wherein the certain direction is a lateral direction in the display region of the display screen.

3. The information processing apparatus according to claim 1, wherein each sliced biological tomographic image, of the plurality of sliced biological tomographic images, includes
a first tomographic image which is a cross section of the sliced biological tomographic image in a first direction,
a second tomographic image which is a cross section of the sliced biological tomographic image in a second direction orthogonal to the first direction, and
a third tomographic image which is a cross section of the sliced biological tomographic image in a third direction orthogonal to the first direction and the second direction.

4. The information processing apparatus according to claim 3, wherein the first tomographic image, the second tomographic image, and the third tomographic image are images of an axial view, a sagittal view, and a coronal view, respectively, and are displayed side by side in a vertical direction in the display region of the display screen, and
slices of different sliced biological tomographic images of the two or more sliced biological tomographic images are displayed side by side in a lateral direction in the display region of the display screen.

5. The information processing apparatus according to claim 1, wherein the particular sliced biological tomographic image has a largest quantity of superimposed signal sources among the plurality of sliced biological tomographic images.

6. The information processing apparatus according to claim 5, wherein the particular condition is to display a sliced biological tomographic image having the largest quantity of superimposed signal sources among the plurality of sliced biological tomographic images at a central portion of the display region of the display screen, such that the particular sliced biological tomographic image is displayed at the central portion of the display region of the display screen in accordance with the particular condition.

7. The information processing apparatus according to claim 6, wherein the display control unit is further configured to arrange and display, in the display region of the display screen, the other sliced biological tomographic images of the two or more sliced biological tomographic images such that the other sliced biological tomographic images are arranged in order of layers laterally from the particular sliced biological tomographic image that is displayed at the central portion of the display region of the display screen according to the particular condition.

8. The information processing apparatus according to claim 1, wherein the display control unit is further configured to divide the plurality of sliced biological tomographic images into groups that each include a particular quantity of sliced biological tomographic images that are sliced in the particular direction, each group associated with a separate sum of quantities of superimposed signal sources corresponding to the particular quantity of sliced biological tomographic images included in the group, such that the groups are associated with separate, respective sums of quantities of superimposed signal sources, and
the particular sliced biological tomographic image is included in a particular group, of the groups, associated with a largest sum of the separate, respective sums of quantities of superimposed signal sources.

9. The information processing apparatus according to claim 1, wherein the display control unit is configured to also display, in the display region of the display screen, one or more sliced biological tomographic images, of the plurality of sliced biological tomographic images, on which no signal source is superimposed.

10. The information processing apparatus according to claim 1, wherein the display control unit is configured to selectively not display, in the display region of the display screen, one or more sliced biological tomographic images, of the plurality of sliced biological tomographic images on which no signal source is superimposed in response to a command.

11. The information processing apparatus according to claim 1, wherein the display control unit is configured to cause the display device to display information indicating a quantity of superimposed signal sources together with a corresponding sliced biological tomographic image, of the two or more sliced biological tomographic images displayed in the display region.

12. The information processing apparatus according to claim 1, wherein the display control unit is configured to cause the display device to display information indicating a tomographic position of a separate sliced biological tomographic image, of two or more biological tomographic images displayed in the display region.

13. An information processing method, the method comprising:
   performing control to
   display, in a region of an analysis screen displayed by a display device, one or more signal sources in a superimposed manner on a plurality of sliced biological tomographic images, of a brain of a human subject, that are sliced in a particular direction, each signal source corresponding to a part of biological data indicating a temporal change of a biological signal and representing a dipole estimation result determined based on the biological data, each signal source superimposed at a particular position on at least one sliced biological tomographic image to indicate a point position associated with the signal source in an image portion of the brain of the human subject that is shown in the at least one sliced biological tomographic image, and
   display, in a display region of a display screen displayed by the display device, two or more sliced biological tomographic images of the plurality of sliced biological tomographic images, such that the two or more sliced biological tomographic images are arranged in a certain direction in the display region of the display screen,
   wherein the two or more sliced biological tomographic images include a particular sliced biological tomographic image, of the plurality of sliced biological tomographic images, that is displayed in the display region in accordance with a particular condition, and other sliced biological tomographic images of the two or more sliced biological tomographic images are arranged in the certain direction in relation to the particular sliced biological tomographic image in the display region of the display screen.

14. The information processing method according to claim 13, wherein
   the particular sliced biological tomographic image has a largest quantity of superimposed signal sources among the plurality of sliced biological tomographic images.

15. The information processing method according to claim 14, wherein
   the particular condition is to display a sliced biological tomographic image having the largest quantity of superimposed signal sources among the plurality of sliced biological tomographic images at a central portion of the display region of the display screen, such that the particular sliced biological tomographic image is displayed at the central portion of the display region of the display screen in accordance with the particular condition.

16. The information processing method according to claim 15, further comprising:
   arranging and displaying, in the display region of the display screen, the other sliced biological tomographic images of the two or more sliced biological tomographic images such that the other sliced biological tomographic images are arranged in order of layers laterally from the particular sliced biological tomographic image that is displayed at the central portion of the display region of the display screen.

17. A non-transitory computer-readable medium including programmed instructions that cause a computer to execute a method, the method comprising:
   performing control to
   display, in a region of an analysis screen displayed by a display device, one or more signal sources in a superimposed manner on a plurality of sliced biological tomographic images, of a brain of a human subject, that are sliced in a particular direction, each signal source corresponding to a part of biological data indicating a temporal change of a biological signal and representing a dipole estimation result determined based on the biological data, each signal source superimposed at a particular position on at least one sliced biological tomographic image to indicate a point position associated with the signal source in an image portion of the brain of the human subject that is shown in the at least one sliced biological tomographic image, and
   display, in a display region of a display screen displayed by the display device, two or more sliced biological tomographic images of the plurality of sliced biological tomographic images, such that the two or more sliced biological tomographic images are arranged in a certain direction in the display region of the display screen,
   wherein the two or more sliced biological tomographic images include a particular sliced biological tomographic image, of the plurality of sliced biological tomographic images, that is displayed in the display region in accordance with a particular condition, and other sliced biological tomographic images of the two or more sliced biological tomographic images are arranged in the certain direction in relation to the particular sliced biological tomographic image in the display region of the display screen.

18. The non-transitory computer-readable medium according to claim 17, wherein
   the particular sliced biological tomographic image has a largest quantity of superimposed signal sources among the plurality of sliced biological tomographic images.

19. The non-transitory computer-readable medium according to claim 18, wherein
   the particular condition is to display a sliced biological tomographic image having the largest quantity of superimposed signal sources among the plurality of sliced biological tomographic images at a central portion of the display region of the display screen, such that the particular sliced biological tomographic image is displayed at the central portion of the display region of the display screen in accordance with the particular condition.

20. The non-transitory computer-readable medium according to claim 19, the method further comprising:
   arranging and displaying, in the display region of the display screen, the other sliced biological tomographic images of the two or more sliced biological tomographic images such that the other sliced biological tomographic images are arranged in order of layers laterally from the particular sliced biological tomographic image that is displayed at the central portion of the display region of the display screen.

* * * * *